US010738274B2

(12) United States Patent
Mogna et al.

(10) Patent No.: US 10,738,274 B2
(45) Date of Patent: Aug. 11, 2020

(54) MULTILAYER MICROENCAPSULATED PROBIOTIC BACTERIA

(71) Applicant: PROBIOTICAL NORTH AMERICA INC., Chicago, IL (US)

(72) Inventors: Giovanni Mogna, Novara (IT); Luca Mogna, Novara (IT)

(73) Assignee: PROBIOTICAL NORTH AMERICA INC., Chicago, IL (US)

( * ) Notice: Subject to any disclaimer, the term of this patent is extended or adjusted under 35 U.S.C. 154(b) by 635 days.

(21) Appl. No.: 14/376,268

(22) PCT Filed: Feb. 1, 2013

(86) PCT No.: PCT/IB2013/000124
§ 371 (c)(1),
(2) Date: Aug. 1, 2014

(87) PCT Pub. No.: WO2013/114185
PCT Pub. Date: Aug. 8, 2013

(65) Prior Publication Data
US 2014/0370107 A1    Dec. 18, 2014

(30) Foreign Application Priority Data

Feb. 1, 2012   (IT) .............................. MI2012A0131

(51) Int. Cl.
| | |
|---|---|
| *C12N 1/20* | (2006.01) |
| *A23C 9/16* | (2006.01) |
| *A23C 15/12* | (2006.01) |
| *A23G 3/34* | (2006.01) |
| *A23C 13/16* | (2006.01) |
| *A23C 9/12* | (2006.01) |
| *A23C 19/086* | (2006.01) |
| *A23L 21/10* | (2016.01) |
| *A23P 10/35* | (2016.01) |
| *A23L 33/135* | (2016.01) |
| *A23C 9/152* | (2006.01) |
| *A23C 19/14* | (2006.01) |
| *A23G 3/36* | (2006.01) |
| *A61K 9/14* | (2006.01) |
| *A61K 35/745* | (2015.01) |
| *A61K 9/50* | (2006.01) |
| *A61K 35/741* | (2015.01) |
| *A61K 35/00* | (2006.01) |

(52) U.S. Cl.
CPC .................. *C12N 1/20* (2013.01); *A23C 9/12* (2013.01); *A23C 9/152* (2013.01); *A23C 9/16* (2013.01); *A23C 13/16* (2013.01); *A23C 15/123* (2013.01); *A23C 19/086* (2013.01); *A23C 19/14* (2013.01); *A23G 3/346* (2013.01); *A23G 3/366* (2013.01); *A23L 21/10* (2016.08); *A23L 33/135* (2016.08); *A23P 10/35* (2016.08); *A61K 9/14* (2013.01); *A61K 35/745* (2013.01); *A23V 2002/00* (2013.01); *A23V 2200/00* (2013.01); *A23Y 2220/73* (2013.01); *A23Y 2300/29* (2013.01); *A61K 9/5073* (2013.01); *A61K 35/741* (2013.01); *A61K 2035/115* (2013.01)

(58) Field of Classification Search
CPC ............ A23G 2200/02; A23G 2220/20; A23G 3/366; A23L 1/3014; A23L 1/0032; A23L 1/30; A61K 35/741; A61K 35/745; A61K 2035/115; A61K 9/5073; A61K 35/74; A61K 9/14; A23C 15/123; C12N 1/02; C12N 1/20
USPC .................................. 424/490, 93.4; 426/61
See application file for complete search history.

(56) References Cited

U.S. PATENT DOCUMENTS

| | | | | |
|---|---|---|---|---|
| 6,676,933 B2* | 1/2004 | Vergez | ............... | A61K 31/5375 424/78.01 |
| 2007/0135379 A1* | 6/2007 | Mallard | ................... | A61K 8/67 514/63 |
| 2009/0162322 A1* | 6/2009 | Rudolph | .............. | A61K 9/2009 424/93.4 |

(Continued)

FOREIGN PATENT DOCUMENTS

| | | |
|---|---|---|
| WO | 93/19162 | 9/1993 |
| WO | 2010/103374 | 9/2010 |
| WO | 2010/138552 | 12/2010 |

(Continued)

OTHER PUBLICATIONS

Zambiazi et al. Fatty Acid Composition of Vegetable Oils and Fats, B.CEPPA, Curitiba, vol. 25, pp. 111-120.*

(Continued)

Primary Examiner — Thane Underdahl
(74) Attorney, Agent, or Firm — Steinfl + Bruno, LLP

(57) ABSTRACT

A multilayer microencapsulated lactic bacteria and bifidobacteria, preferably bacteria with probiotic activity, and the use thereof to prepare a food product, supplement product, medical device or pharmaceutical composition or water- and/or fruit-based beverage are described. A process for preparing multilayer microencapsulated lactic bacteria and bifidobacteria, preferably bacteria with probiotic activity is described. A food product is described selected from water, water- and/or fruit-based beverages, milk, fresh whole milk, partially skimmed milk, powdered milk, cheese, fresh cheese, aged cheese, grated cheese, butter, margarine, yogurt, cream, milk- and chocolate-based custards, custards for sweets, jams and oily suspensions having bacteria, preferably multilayer microencapsulated lactic bacteria and bifidobacteria with probiotic activity.

20 Claims, 3 Drawing Sheets

(56) References Cited

U.S. PATENT DOCUMENTS

2012/0021095 A1   1/2012   Mogna et al.

FOREIGN PATENT DOCUMENTS

| WO | WO 2011029784 | * | 3/2011 |
| WO | 2012/021432 |   | 2/2012 |
| WO | WO 2012021432 | * | 2/2012 |

OTHER PUBLICATIONS

STN Search results for CAS No. 85251-77-0 and 61725-93-7, accessed Mar. 23, 2018, 3 pgs.*
STN, Entry for "CAS 85251-77-0", STN 1 pgs. 2020 (Year: 2020).*
PCT International Search Report dated Jun. 3, 2013 for PCT Application No. PCT/IB2013/00124 filed on Feb. 1, 2013 in the name of Probiotical S.P.A.
PCT Written Opinion dated Jun. 3, 2013 for PCT Application No. PCT/IB2013/00124 filed on Feb. 1, 2013 in the name of Probiotical S.P.A.
Evonik Industries AG, *GSP Safety Summary*, Technical Information, Glycerides, C16-18 mono- and di- CAS-No. 85251-77-0;Nov. 2010, Version 1, 6 pages.
Glycerides, C16-18 mono-and di-; C37H7205—PubChem; 1 page.
International Preliminary Report on Patentability for International Application No. PCT/IB2013/000124 filed on Feb. 1, 2013 on behalf of Probiotical S.P.A.; dated Aug. 5, 2014 7 pages.
Polyglyceryl-6 Distearate CAS-61725-93-7, Parchem Fine & Specialty Chemicals; https://www.parchem.com/chemical-supplier-distributor/polyglyceryl-6-distearate-096812.aspx 2018; 5 pages.
Wikipedia page of Food Additive (Italian + English Translation).

* cited by examiner

MULTILAYER MICROENCAPSULATED PROBIOTIC BACTERIA

CROSS REFERENCE TO RELATED APPLICATIONS

The present application is the US national stage of International Patent Application PCT/IB2013/000124 filed on Feb. 1, 2013 which, in turn, claims priority to Italian Patent Application MI2012A000131 filed on Feb. 1, 2012.

The present invention relates to lactic bacteria and bifidobacteria, preferably multilayer microencapsulated bacteria with probiotic activity, and the use thereof to prepare a food product, supplement product, medical device or pharmaceutical composition or water- and/or fruit-based beverage. Moreover, the present invention relates to a process for preparing lactic bacteria and bifidobacteria, preferably multilayer microencapsulated bacteria with probiotic activity. In particular, the present invention relates to a food product selected from among water, water- and/or fruit-based beverages, milk, fresh whole milk, partially skimmed milk, powdered milk, cheese, fresh cheese, aged cheese, grated cheese, butter, margarine, yogurt, cream, milk- and chocolate-based custards, custards for sweets, jams and oily suspensions comprising bacteria, preferably multilayer microencapsulated lactic bacteria and bifidobacteria with probiotic activity.

The presence on the market of food products such as, for example, chocolate and yogurt, or supplement products such as, for example, nutritional supplements or products in the form of an oily suspension, all containing probiotic bacteria, is well known. However, said finished products exhibit some drawbacks which limit their effectiveness and use.

A first drawback relates to the stability of the bacteria present within a finished product. In practical terms, the lactic bacteria or bifidobacteria present, for example, in a finished food product suffer from low or reduced stability. The low or reduced stability is due to the environment in which the bacteria are situated. The low or reduced stability in general causes a decline in the concentration of bacteria present in the finished product over time. In practical terms, a given initial concentration of bacteria declared at t0 for a given finished product declines over time because of the low stability of the bacteria themselves within said finished product.

Therefore, the initial concentration of bacteria present (at t(0), initial time of manufacture of the finished product) in the finished product does not correspond, already after a certain relatively brief interval of time after the manufacturing date, to the concentration of bacteria declared on the label, due to the decline in the concentration of bacteria that occurs over said interval of time.

To increase stability it has been proposed to coat or microencapsulate (cover) the bacteria with a coating.

However, there does not exist at present a coating or microencapsulation or covering technology capable of imparting stability to the bacteria irrespective of the nature of the finished product they will be added to, the chemical and physical properties of the finished product, the water content present in the ingredients, excipients and additives used to formulate the finished product, and the physical state of the finished product, which can be, for example, solid, in powder or granular form, liquid or in a suspension.

Therefore, it would be desirable to have a technology for coating or microencapsulating or covering the bacteria which enables the coated or microencapsulated (covered) bacteria to be prepared in such a way that said coated or microencapsulated bacteria can be used to prepare any finished product irrespective of the nature of the finished product they will be added to, the chemical and physical properties of the finished product, the water content present in the ingredients, excipients and additives used to formulate the finished product, and the physical state of the finished product, which can be, for example, solid, in powder or granular form, liquid or in a suspension.

A second drawback relates to the nature of the ingredients, excipients and additives used to formulate and prepare the finished product, such as, for example, the pH value, the free water content and the chemical composition from a qualitative and quantitative viewpoint. All of these factors, besides influencing the viability of the bacteria, can condition/modify their effectiveness once administered into the body (in vivo viability and functionality) and, consequently, prejudice their ability to colonize the intestine. In this regard it is very important to stress that the bacteria must be protected during gastric and duodenal transit, otherwise they will arrive in the intestine in a greatly reduced number and in a hardly viable state for multiplying in sufficient number.

Therefore, it would be desirable to have a technology for coating or microencapsulating (covering) bacteria which enables the coated or microencapsulated (covered) bacteria to be prepared in such a way that said coated or microencapsulated bacteria can acquire the necessary resistance enabling them to pass through gastric and duodenal transit intact.

A third drawback relates to the fact that the coatings used to coat or cover the bacteria are not such as to ensure a sufficient endurance or resistance to mechanical friction stresses that occur during mixing of the bacteria with the ingredients, excipients and additives used in the formulation of the final product. In practical terms, it often occurs that the coatings used to coat the bacteria suffer from mechanical stresses or friction that are created during the processing steps, for example during mixing of the bacteria with the various ingredients, excipients and additives necessary to formulate a finished product, be it a food product, a supplement product, a medical device or a pharmaceutical composition. The consequence is that an erosion occurs which weakens the coating, causing it to lose consistency and structure. Moreover, micro fractures (cracks) are created on the outer part of the coating, which allows the passage of humidity and substances that are toxic for the bacteria. The consequence is a loss of stability and viability and a low or reduced colonization.

Finally, there are also several considerations to be made concerning the stability of the food product itself. In practical terms, after a certain time interval, the lactic bacteria placed within a food product can give rise to precipitation phenomena and/or aggregation phenomena with the subsequent formation of a bacterial aggregate or a precipitate. These phenomena can alter the shelf life of the food product.

Therefore, there remains a need to be able to have a finished product (food product or a medical device or a supplement product or a pharmaceutical composition) comprising lactic bacteria or bifidobacteria, preferably bacteria with probiotic activity, having an improved shelf stability compared to the finished products present on the market.

There remains a need in particular to be able to have a finished product (food product or a medical device or a supplement product or a pharmaceutical composition) comprising lactic bacteria or bifidobacteria, preferably with probiotic activity, in which the concentration of bacteria initially present is not subject to a decline over time such as to lead to a drastic reduction in the concentration of bacteria initially estimated at time t(0), the time of the product's manufacture.

Finally, it is necessary for the food product containing the probiotic bacteria to be prepared in such a way as to maintain the bacteria in a good state of viability and functionality in order to ensure sufficient colonization also if the coated bacteria are placed in contact, in the formulation, with substances of a toxic character or antibiotics.

After intense research activity, the Applicant has provided an answer to the above-mentioned needs by developing a technology for coating or microencapsulating (covering) bacteria which makes it possible to produce coated or microencapsulated (covered) bacteria that do not exhibit the drawbacks of the prior art.

The subject matter of the present invention relates to multilayer coated or microencapsulated bacteria, as claimed in the appended claim.

The subject matter of the present invention relates to a method for preparing the multilayer coated or microencapsulated bacteria, as claimed in the appended claim.

The subject matter of the present invention relates to a finished product (food product or a medical device or a supplement product or a pharmaceutical composition) comprising the multilayer coated or microencapsulated bacteria, as claimed in the appended claim.

The subject matter of the present invention relates to the use of the multilayer coated or microencapsulated bacteria to prepare a finished product (food product or a medical device or a supplement product or a pharmaceutical composition), as claimed in the appended claim.

Figure 1:
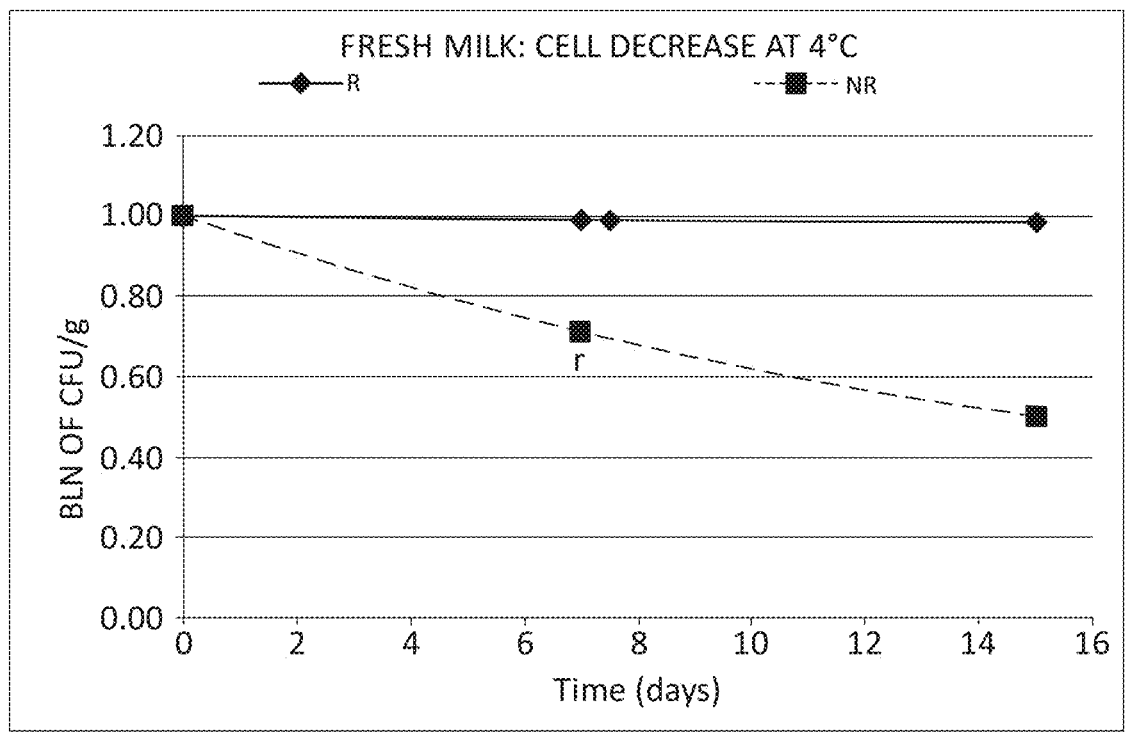
FIG. 1 shows a stability analysis of a sample of fresh milk supplemented with bacteria of the strain *Lactobacillus rhamnosus* GG (ATCC53103) at 4°C. for 7 and 14 days.

Preferred embodiments of the present invention are set forth in the detailed description that follows, which is presented by way of example, therefore without limiting the scope of the invention.

The Applicant has found that the coating to be applied externally to the bacteria (bacterial cells) must not be formed of a single coating (or covering) layer but, on the contrary, it must be formed of at least two coating layers. The formation of a coating consisting of a single layer does not fall within the context of the present invention. The coating layers that are formed on the bacteria are in a number "n" comprised from 2 to 10; preferably "n" is comprised from 3 to 9; advantageously "n" is equal to 3, or 4, or 5, or 6, or 7, or 8.

A given amount "X" by weight of bacteria, having a concentration expressed in CFU/g, is coated or microencapsulated with a given amount "Y" by weight of a coating material comprising lipids of vegetable origin. The amount by weight Y can be less than, equal to or greater than X. The ratio by weight Y:X, relative to the final weight of the coated bacteria, can be, for example, 1:1, or 1,25:1, or 1,50:1, or 1,75:1, or 2:1. The amount Y is applied in a number "n" of layers or coatings, where in each layer or coating the amount by weight applied is equal to Y/n.

For example, 100 grams of bacteria ("X") having a concentration of $200 \times 10^9$ CFU/g can be coated or microencapsulated with 100 grams ("Y") of coating material. In this case Y is equal to X. The 100 grams ("Y") of coating material are not applied to the bacteria in a single coating or microencapsulation step in order to yield bacteria with a single layer or coating (mono-coated bacteria). On the contrary, the 100 grams ("Y") of coating material are applied on the bacteria in a number "n" of coating layers. For each coating layer that is formed, the amount of coating material applied is equal to Y/n. The coated or microencapsulated bacteria that are obtained are multilayer coated or multi-coated bacteria. The value of "n" is fixed a priori according to the properties it is desired to impart to the coated bacteria, which depends on the chemical and physical properties of the finished product they will be added to, the type of processing necessary to formulate the finished product, the water content present in the finished product, ingredients, excipients and additives used to formulate the finished product, the physical state of the finished product or the presence of toxic or antibiotic substances.

The types of lipids to be used also depend on the chemical and physical properties of the finished product the coated bacteria will be added to, the type of processing necessary to formulate the finished product, the water content present in the finished product, ingredients, excipients and additives used to formulate the finished product, the physical state of the finished product or the presence of toxic or antibiotic substances.

In this example, the 100 grams ("Y") of coating material can be applied on the bacteria in two steps (n=2). Therefore, in each layer or coating the amount applied is equal to Y/n, i.e. 50 grams. The 100 grams ("Y") of coating material can be applied on the bacteria as follows: 60 grams (first layer)+40 grams (second layer) or, alternatively, 80 grams (first layer)+20 grams (second layer). At the end of the coating or microencapsulation process 200 grams of bacteria coated with two layers will be obtained, at a concentration of $100 \times 10^9$ CFU/g.

In this example, the 100 grams ("Y") of coating material can be applied on the bacteria in three steps (n=3). Therefore, in each layer or coating the amount applied is equal to Y/n, i.e. 33.3 grams. The 100 grams ("Y") of coating material can also be applied on the bacteria as follows: 40 grams (first layer)+40 grams (second layer)+20 grams (third layer) or, alternatively, 50 grams (first layer)+25 grams (second layer)+25 grams (third layer). At the end of the coating or microencapsulation process 200 grams of bacteria coated with three layers will be obtained, at a concentration of $100 \times 10^9$ CFU/g.

Alternatively, for example, the 100 grams ("Y") of coating material can be applied on the bacteria in four steps (n=4). Therefore, in each layer or coating the amount applied is equal to Y/n, i.e. 25 grams. The 100 grams ("Y") of coating material can also be applied on the bacteria as follows: 30 grams (first layer)+20 grams (second layer)+30 grams (third layer)+20 grams (fourth layer), or, alternatively, 40 grams (first layer)+20 grams (second layer)+20 grams (third layer)+20 grams (fourth layer). At the end of the coating or microencapsulation process 200 grams of bacteria coated with four layers will be obtained, at a concentration of $100 \times 10^9$ CFU/g.

Alternatively, for example, the 100 grams ("Y") of coating material can be applied on the bacteria in five steps (n=5). Therefore, in each layer or coating the amount applied is equal to Y/n, i.e. 20 grams. The 100 grams ("Y") of coating material can also be applied on the bacteria as follows: 40 grams (first layer)+15 grams (second layer)+15 grams (third layer)+15 grams (fourth layer)+15 (fifth layer), or, alternatively, 30 grams (first layer)+20 grams (second layer)+20 grams (third layer)+15 grams (fourth layer)+15 grams (fifth). At the end of the coating or microencapsulation process 200 grams of bacteria coated with five layers will be obtained, at a concentration of $100 \times 10^9$ CFU/g.

For example, 100 grams of bacteria ("X") having a concentration of $200 \times 10^9$ CFU/g can be coated with 150 grams ("Y") of coating material. In this case Y is greater than X. The 150 grams ("Y") of coating material can be applied on the bacteria in a number "n" of coating layers, for example, n=3, or 4, or 5.

With n=2, for example, the 150 grams ("Y") of coating material can be applied on the bacteria in two steps (n=2). Therefore, in each layer or coating the amount applied is equal to Y/n, i.e. 75 grams. The 150 grams ("Y") of coating material can also be applied on the bacteria as follows: 100 grams (first layer)+50 grams (second layer) or, alternatively, 80 grams (first layer)+70 grams (second layer). At the end of the coating or microencapsulation process 250 grams of bacteria coated with two layers will be obtained, at a concentration of $80 \times 10^9$ CFU/g.

With n=3, for example, the 150 grams ("Y") of coating material can be applied on the bacteria in three steps (n=3). Therefore, in each layer or coating the amount applied is equal to Y/n, i.e. 50 grams. The 150 grams ("Y") of coating material can also be applied on the bacteria as follows: 75 grams (first layer)+50 grams (second layer)+25 grams (third layer) or, alternatively, 60 grams (first layer)+60 grams (second layer)+30 grams (third layer). At the end of the coating or microencapsulation process 250 grams of bacteria coated with three layers will be obtained, at a concentration of $80 \times 10^9$ CFU/g.

With n=4, for example, the 150 grams ("Y") of coating material can be applied on the bacteria in four steps (n=4). Therefore, in each layer or coating the amount applied is equal to Y/n, i.e. 37.5 grams. The 150 grams ("Y") of coating material can also be applied on the bacteria as follows: 50 grams (first layer)+50 grams (second layer)+25 grams (third layer)+25 grams (fourth layer), or, alternatively, 60 grams (first layer)+30 grams (second layer)+30 grams (third layer)+30 grams (fourth layer). At the end of the coating or microencapsulation process 250 grams of bacteria coated with four layers will be obtained, at a concentration of $80 \times 10^9$ CFU/g.

With n=5, for example, the 150 grams ("Y") of coating material can be applied on the bacteria in five steps (n=5). Therefore, in each layer or coating the amount applied is equal to Y/n, i.e. 30 grams, the 150 grams ("Y") of coating material can also be applied on the bacteria as follows: 50 grams (first layer)+25 grams (second layer)+25 grams (third layer)+25 grams (fourth layer)+25 (fifth layer), or, alternatively, 40 grams (first layer)+30 grams (second layer)+30 grams (third layer)+25 grams (fourth layer)+25 grams (fifth). At the end of the coating or microencapsulation process 250 grams of bacteria coated with five layers will be obtained, at a concentration of $80 \times 10^9$ CFU/g.

The lactic bacteria and bifidobacteria are preferably probiotic bacteria. Probiotic bacteria are live bacteria capable of assuring a beneficial effect to the consumer when taken in large amounts and for an adequate amount of time.

The bacteria are coated or microencapsulated with a coating comprising or, alternatively, consisting of at least one lipid of vegetable origin. The coating is formed of a number of coating layers comprised from 2 to 10, in order to yield a multilayer coating or covering. Advantageously, n is equal to 3, or 4, or 5, or 6.

The probiotic bacteria used in preparing the finished product, in accordance with the present invention, are selected from the group comprising the species: *L. acidophilus, L. crispatus, L. gasseri,* group *L. delbrueckii, L. salivarius, L. casei, L. paracasei,* group *L. plantarum, L. rhamnosus, L. reuteri, L. brevis, L. buchneri, L. fermentum, L. Johnsonii, B. adolescentis, B. angulatum, B. bifidum, B. breve, B. catenulatum, B. infantis, B. lactis, B. longum, B. pseudolongum, B. pseudocatenulatum* and *S. thermophilus.*

The bacteria to be coated or microencapsulated can be in solid form, in particular in powder, granular, dehydrated powder or lyophilized form.

The bacteria are coated or microencapsulated with a coating material comprising or, alternatively, consisting, of at least one lipid of vegetable origin, using techniques and processes known to those skilled in the art.

The individual coating layers are applied/formed with a multilayer coating or microencapsulation or multi-covering technique that envisages the formation of separate layers. The process efficiency for applying/forming a single coating layer is at least 70%, but it is usually comprised from 80 to 90%.

For example, bacteria in lyophilized form can be coated or microencapsulated using a fluid bed technique (for example, top spray or bottom spray) in which the coating material, represented by lipids of vegetable origin, is applied externally on the bacteria after being heated and turned into a liquid state. The coated probiotic bacteria are then added, using known techniques, to the finished product (food product, a supplement product, a medical device or a pharmaceutical composition), for example a food product. The food product is selected from the group comprising milk, whole fresh milk, partially skimmed milk, powdered or freeze-dried milk, cheese, fresh cheese, aged cheese, grated cheese, butter, margarine, yogurt, cream, milk- and chocolate-based custards, custards for sweets, jams and oily suspensions. The food product can also be represented by drinking water or a non-alcoholic beverage. The water or beverage can contain the coated bacteria of the present invention. For example, the coated probiotic bacteria in solid form are gradually added, under stirring, to the finished product, avoiding the formation of lumps and agglomerates. When the addition of bacteria has ended, the product is kept under stirring for a time comprised from 1 to 20 minutes at a temperature comprised from 4 to 18° C. Alternatively, the coated bacteria can be, for example, accommodated in an undercap of a bottle containing water or a beverage, for example orange-flavoured or fruit-flavoured in general. At the time of need, the undercap can be opened and the coated bacteria contained in it will fall into the beverage contained in the bottle.

The bacteria can be mixed by simple stirring with water or with the beverage, which may be orange-flavoured for example.

The coating material comprises or, alternatively, consists of at least one lipid of vegetable origin. The lipids are selected from the group comprising or, alternatively, consisting of saturated vegetable fats having a melting point comprised from 35° C. to 85° C., preferably comprised from 45 to 70° C. Advantageously, from 50 to 60° C.

In a preferred embodiment, saturated vegetable fats having a certain degree of hydrophilicity and/or hydrophobicity can be used; these can be selected from the group comprising mono- and di-glycerides of saturated fatty acids, polyglycerols esterified with saturated fatty acids and free saturated fatty acids.

The saturated fatty acids can be selected from the group comprising from 8 to 32 carbon atoms, preferably 12 to 28 carbon atoms, even more preferably 16 to 24 carbon atoms.

Advantageously, the lipid of natural origin is selected from the group comprising or, alternatively, consisting of:
  (i) Glyceryl dipalmitostearate E471, INCI (PCPC): glyceryl stearate, CAS: 85251-77-0 (or 1323-83-7), EINECS: 286-490-9 (or 215-359-0). Example of a commercial product: Biogapress Vegetal BM 297 ATO-Gattefossé SAS-lipid (i);
  (ii) Polyglyceryl-6-distearate E475, INCI: polyglyceryl-6-distearate, CAS: 61725-93-7. Example of a commercial product: Plurol Stearique WL 1009-Gattefossé SAS-lipid (ii);
  (iii) a mixture of esters of glycerol and fatty acids C16-C18, CAS: 68002-71-1, EINECS: 268-084-3. Example of a commercial product Precirol Ato 5-Gattefossé SAS-lipid (iii);
  (iv) a hydrogenated vegetable fat of non-lauric origin, having a content of free fatty acids calculated as a % of oleic acid, max. 0.20%, a peroxide value of max. 0.20 meqO$_2$/Kg of saturated fatty acids, a minimum solid fat percentage at 20° C. of 94% and a solid fat percentage at 40° C. ranging from a minimum of 94% to a maximum of 99%. Example of a commercial name: Revel C—Loders Croklaan B.V.—lipid (iv).

The type and chemical nature of the lipid used in the coating layer depend on the chemical and physical properties of the finished product, the water content present in the finished product the coated bacteria are added to, the ingredients, excipients and additives used to formulate the finished product, the physical state of the finished product, for example it can be a finished product in an aqueous solution (for example, milk), a finished product in powder or granular form (for example a powdered milk or a grated cheese or butter) or an oily suspension.

In the context of the present invention, "first coating layer" means the coating layer applied externally on surface of the bacteria, whereas "second coating layer" means the coating layer applied externally on said first layer and so forth for the other layers that follow.

The coated bacteria of the present invention are coated or microencapsulated (covered) with a coating comprising or, alternatively, consisting of at least one lipid of vegetable origin. Said coating is a multilayer coating formed of a number of coating layers "n" comprised from 2 to 10. When n=2, the first and the second coating layer comprise or, alternatively, consist of a lipid of vegetable origin which is the same between them; or else when n=2, the first and second coating layer comprise or, alternatively, consist of a lipid of vegetable origin which differs between them; said different lipid is lipid (i). When n is comprised from 3 to 10, the coating layers comprise or, alternatively, consist of at least one lipid of vegetable origin which is the same or differs between them.

The bacteria can be coated or microencapsulated with a coating comprising lipids of vegetable origin. Said coating is formed of a number of coating layers "n" comprised from 2 to 10. When "n" is 2, there are two coating layers. In practical terms, a double coating (two layers) is produced in succession, with two lipids differing from or the same as each other.

When "n" is equal to 2, the first and second coating layer comprise or, alternatively, consist of at least one lipid of vegetable origin which is the same between them. The lipid is selected from the group comprising or, alternatively, consisting, of lipids (i), (ii), (iii) and (iv).

The bacteria can be coated with a first coating layer comprising or, alternatively, consisting of lipid (i) and a second coating layer comprising or, alternatively, consisting of lipid (i). The ratio by weight between said first and second coating layer is comprised from 1:3 to 3:1, preferably 1:2 to 2:1, or 1:1.

The bacteria can be coated with a first coating layer comprising or, alternatively, consisting of lipid (ii) and a second coating layer comprising or, alternatively, consisting of lipid (ii). The ratio by weight between said first and second coating layer is comprised from 1:3 to 3:1, preferably 1:2 to 2:1, or 1:1.

When "n" is equal to 2, the first and second coating layer comprise or, alternatively, consist of at least one lipid of vegetable origin which differs between them. In this case said different lipid is lipid (i). Whereas the second lipid is selected from the group comprising or, alternatively, consisting, of lipids (ii), (iii) and (iv).

The bacteria can be coated with a first coating layer comprising or, alternatively, consisting of lipid (i) and a second coating layer comprising or, alternatively, consisting of lipid (ii), or (iii), or (iv). The ratio by weight between said first and second coating layer is comprised from 1:3 to 3:1, preferably 1:2 to 2:1, or 1:1.

The bacteria can be coated with a first coating layer comprising or, alternatively, consisting of lipid (ii), or (iii), or (iv) and a second coating layer comprising or, alternatively, consisting of lipid (i). The ratio by weight between said first and second coating layer is comprised from 1:3 to 3:1, preferably 1:2 to 2:1, or 1:1.

Irrespective of the specific type of lipid used, the two lipids are sprayed onto the lyophilized bacteria in succession, i.e. a double covering is applied on the lyophilizate, consisting of a first coating layer (the coating layer applied externally on the surface of the bacteria) and a second coating layer (the coating layer applied externally on said first layer). Between said first and said second coating layer, a pause is made in order to let the bacteria with the first coating layer cool and enable the coating to solidify. Subsequently, the second coating layer is applied. The lipid to be applied is heated to the melting temperature in order to obtain a sprayable liquid form and, at that temperature, is applied on the lyophilized bacteria.

The bacteria can be coated or microencapsulated with three coating layers. In practical terms, a coating with three lipids different from or the same as each other (triple coating or triple layer) is produced in succession.

The bacteria can be coated with a first and second layer of lipid (i) and then a third layer of lipid (ii), or with a first and second layer of lipid (ii) and a third layer of lipid (i).

Advantageously, the stability that is achieved is maintained over time with the coated bacteria of the present invention; in particular, in an environment that is highly unfavourable to bacteria, such as that represented by water or very moist powders, it enables water- or water and fruit-based beverages to be successfully prepared.

Moreover, the coated bacteria of the present invention enable the probiotic bacteria to be formulated in an intimate mixture with antibiotics so as to prepare, for example, a capsule containing coated probiotic bacteria and antibiotics for simultaneous administration. In this manner we are able to assure that the bacteria resist the gastric barrier and the presence of antibiotics and are able to arrive intact in the intestine and colonize so as to restore the balance of bacterial flora devastated by the effect of the antibiotic.

The subject matter of the present invention also relates to a pharmaceutical composition comprising the coated lyophilized bacteria of the present invention and at least one pharmaceutical active ingredient with antibiotic activity; preferably an antibiotic can be selected from the group comprising, among others, ciprofloxacin, erythromycin or ampicillin.

The Applicant conducted a series of experimental trials, the results of which are reported below.

Table A shows, by way of example, a group of microorganisms that have valid application in the context of the present invention. All of the strains were deposited in accordance with the Budapest Treaty and are made accessible to the public, on request, by the competent Depositing Authority. The depositing Authorities include the National Collection of Microorganisms Cultures (CNCM I.P.) having an address of Institut Pasteur, 25-28 rue du Docteur Roux, 75724 Paris, France, Belgian Coordinated Collections of Microorganisms/Laboratorium voor Microbiologie (BCCM LMG) having an address of Universiteit Gent, K. L. Ledeganckstraat 35, B-9000, Gent, Belgium, and Deutsche Sammlung von Mikroorganismen and Zellkulturen GmbH (DSMZ) having an address of Inhoffenstrasse 7B, D-38124, Braunschweig, Germany.

The Applicant conducted experimental trials in vivo and in vitro in order to evaluate the stability and resistance to gastric juices, pancreatic juices and bile salts of the bacteria coated with two, three and four coating layers comprising the above-mentioned lipids (i), (ii), (iii) and (iv). The tests conducted confirm that the coated bacteria (gastro-protected) are capable of withstanding the attack of gastric and pancreatic juices and bile salts and are therefore capable of arriving in the intestine live and viable and at a concentration identical to the initial one present in the product at the time of preparation.

1) Stability analysis of 3 bacterial samples of *Lactobacillus rhamnosus* GG (ATCC53103) in water at 25° C. for 4 days, Table 1.

Sample 1: 100 grams of *Lactobacillus rhamnosus* GG (ATCC53103) at a concentration of 200 CFU/g are coated with a coating layer consisting of 100 grams of lipid (ii). Ratio by weight of lyophilized bacteria:lipid (ii)=1:1— (mono coating).

Sample 2: 100 grams of *Lactobacillus rhamnosus* GG (ATCC53103) at a concentration of 200 CFU/g are coated with a coating layer consisting of 100 grams of lipid (i). Ratio by weight lyophilized bacteria:lipid (i)=1:1—(mono coating).

Sample 3: 100 grams of *Lactobacillus rhamnosus* GG (ATCC53103) at a concentration of 200 CFU/g are coated with two coating layers: the first coating layer consists of 50 grams of lipid (i), whereas the second coating layer consists of 50 grams of lipid (ii)—(double coating). Ratio by weight of lyophilized bacteria:lipid (i)+(ii)=1:1—(double coating).

The coated bacteria (samples 1, 2 and 3) were placed in water in a quantity such as to ensure a concentration of $5 \times 10^9$ CFU/10 ml. The suspensions obtained were stored at 25° C. in glass vials.

TABLE 1

|  | BLN/g expected | BLN/g obtained | BLN/g 4 days 25° C. | % mortality 4 days 25° C. |
|---|---|---|---|---|
| Sample 1 LGG + lipid (ii) Mono coating | | | | |
| Total | 0.71 | 0.24 | 0.021 | 97.04 |
| Free | 0.21 | 0.26 | 0.019 | 90.95 |
| Coated | 0.5 | | 0.002 | 99.6 |
| coating % | 70 | Nd | 9.5 | |
| Sample 2 LGG + lipid (i) Mono coating | | | | |
| Total | 0.65 | 0.38 | 0.23 | 64.62 |
| Free | 0.15 | 0.09 | 0.017 | 88.67 |
| Coated | 0.5 | 0.29 | 0.213 | 57.40 |
| coating % | 77 | 76 | 92 | |
| Sample 3 LGG + lipid (i) + (ii) Double coating | | | | |
| Total | 0.62 | 0.63 | 0.58 | 6.45 |
| Free | 0.12 | 0.15 | 0.09 | 25.00 |
| Coated | 0.5 | 0.48 | 0.49 | 2.00 |
| coating % | 81 | 76 | 84 | |

Table 1 shows that with an equal amount of coating material used (Y), in this case 100 grams, the formation of two coating layers surprisingly imparts a higher stability to the cells of the coated bacteria.

2) Stability analysis of a bacterial sample of *Lactobacillus rhamnosus* GG (ATCC53103) in water at 25° C. for 14 days, Table 2.

A sample like the one in the above trial, sample 3, was tested in water at 25° C. for 14 days. Sample 3: 100 grams of *Lactobacillus rhamnosus* GG (ATCC53103) at a concentration of 200 CFU/g are coated with two coating layers: the first coating layer consists of 50 grams of lipid (i), whereas the second coating layer consists of 50 grams of lipid (ii)—(double coating). Ratio by weight of lyophilized bacteria:lipid (i)+(ii)=1:1—(double coating).

The coated bacteria (sample 3) were placed in water in a quantity such as to ensure a concentration of $5 \times 10^9$ CFU/10 ml. The suspensions obtained were stored at 25° C. in glass vials.

TABLE 2

| Sample 3 | BLN/g expected | BLN/g obtained | BLN/g 4 days 25° C. | BLN/g 14 days 25° C. |
|---|---|---|---|---|
| Total | 0.62 | 0.63 | 0.58 | 0.56 |
| Free | 0.12 | 0.15 | 0.09 | 0.80 |
| Coated | 0.50 | 0.48 | 0.49 | 0.48 |
| coating % | 81 | 76 | 84 | 86 |

Table 2 shows that in an aqueous environment (highly unfavourable to bacteria), the double coating imparts excellent stability, also for a very long period of time such as 14 days. The results of Table 2 confirm those shown in Table 1.

3) Stability analysis of a sample of powdered milk supplemented with bacteria of the strain *Bifidobacterium breve* BR03 (DSM 16604) at 25° C. for 60 days, Table 3.

Sample a: Powdered milk+uncoated lyophilized bacteria ("naked" cells) of the strain *Bifidobacterium breve* BR03 (DSM 16604) —NR.

Sample b: Powdered milk+bacteria of *Bifidobacterium breve* BR03 (DSM 16604). 100 grams of the strain *Bifidobacterium breve* BR03 (DSM 16604) at a concentration of 200 CFU/g are coated with two coating layers —R: the first coating layer consists of 50 grams of lipid (i), whereas the second coating layer consists of 50 grams of lipid (i)—(double coating). Ratio by weight of lyophilized bacteria: lipid (i)+(i)=1:1—(double coating). The coated bacteria (sample (b)) were mixed with powdered milk and stored at 25° C. for 60 days.

TABLE 3

| Sample | T0 BLN/g | 24 days at 25° C. BLN/g | 24 days at 25° C. t/2 | 60 days at 25° C. BLN/g | 60 days at 25° C. t/2 |
| --- | --- | --- | --- | --- | --- |
| Sample (a) | 13.5 | 10.3 | 61.5 | 7 | 63.3 |
| Sample (b) | 3.2 | 3 | 257.8 | 2.9 | 422.5 |

4) Stability analysis of a sample of fresh milk supplemented with bacteria of the strain *Lactobacillus rhamnosus* GG (ATCC53103) at 4° C. for 7 and 14 days, Table 4 and FIG. 1.

Sample 4a: Fresh milk+uncoated lyophilized bacteria ("naked" cells) of the strain *Lactobacillus rhamnosus* GG (ATCC53103) —NR.

Sample 4b: Fresh milk+bacteria of the strain *Lactobacillus rhamnosus* GG (ATCC53103). 100 grams of *Lactobacillus rhamnosus* GG (ATCC53103) at a concentration of 200 CFU/g are coated with two coating layers —R: the first coating layer consists of 50 grams of lipid (i), whereas the second coating layer consists of 50 grams of lipid (i)—(double coating). Ratio by weight of lyophilized bacteria: lipid (i)+(i)=1:1—(double coating). The coated bacteria (sample (4b)) were mixed with fresh milk and stored at 4° C. for 7 and 14 days.

TABLE 4

| Fresh milk (shelf life 4 days) | T0 | 7 days | 1 day |
| --- | --- | --- | --- |
| | Viable cells (Billions BLN/CFUxg) | | |
| Sample 4(b) | 1.00 | 0.99 | 0.985 |
| Sample 4(a) | 1.00 | 0.71 | 0.50 |

Figure 2:
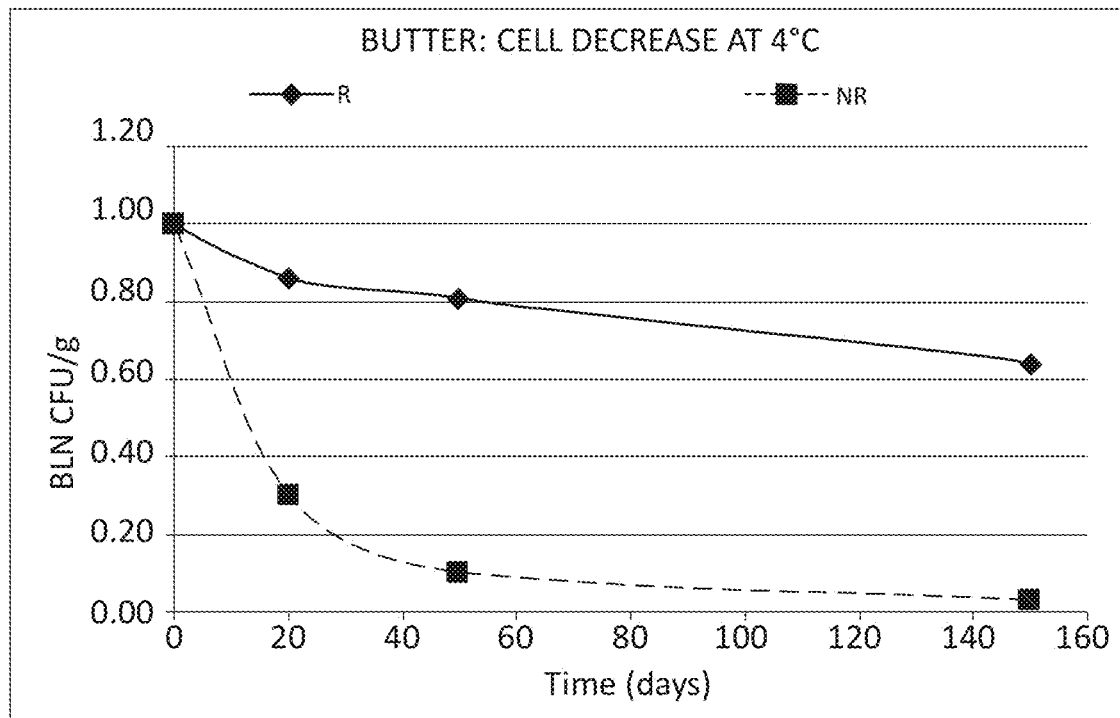
FIG. 2 shows a stability anaylsis of a sample of butter supplemented with bacteria of the strain *Lactobacillus rhamnosus* GG (ATCC53103) at 4°C. for 20, 50 and 150 days.

5) Stability analysis of a sample of butter supplemented with bacteria of the strain *Lactobacillus rhamnosus* GG (ATCC53103) at 4° C. for 20, 50 and 150 days, Table 5 and FIG. 2.

Sample 5a: Butter+uncoated lyophilized bacteria ("naked" cells) of the strain *Lactobacillus rhamnosus* GG (ATCC53103) —NR.

Sample 5b: Butter+bacteria of the strain *Lactobacillus rhamnosus* GG (ATCC53103). 100 grams of *Lactobacillus rhamnosus* GG (ATCC53103) at a concentration of 200 CFU/g are coated with two coating layers —R: the first coating layer consists of 50 grams of lipid (ii), whereas the second coating layer consists of 50 grams of lipid (ii)—(double coating). Ratio by weight of lyophilized bacteria: lipid (ii)+(ii)=1:1—(double coating). The coated bacteria (sample (5b)) were mixed with fresh butter and stored at 4° C. for 20, 50 and 150 days.

TABLE 5

| Butter (shelf life 90 days) | T0 | 20 days | 50 days | 150 days |
| --- | --- | --- | --- | --- |
| | Viable cells (Billions BLN/CFUxg) | | | |
| Sample 5(b) | 1.00 | 0.86 | 0.81 | 0.640 |
| Sample 5(a) | 1.00 | 0.30 | 0.10 | 0.03 |

Figure 3:
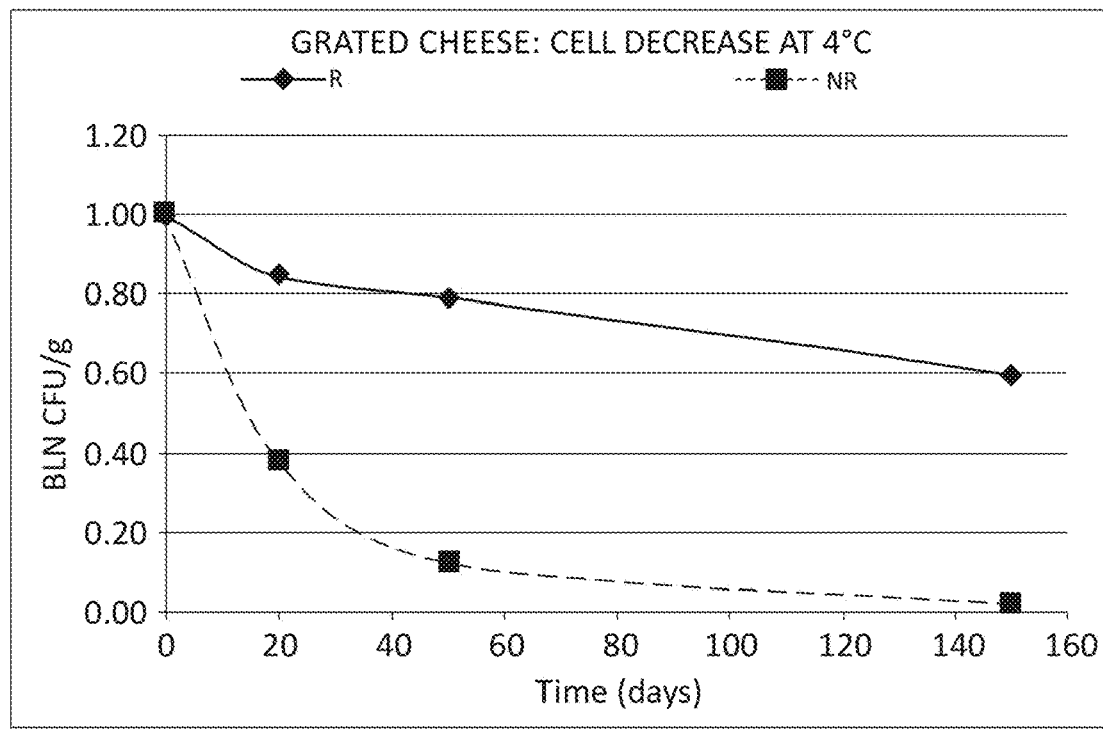
FIG. 3 shows a stability anaylsis of a sample of grated cheese supplemented with bacteria of the strain *Lactobacillus rhamnosus* GG (ATCC53103) at 4°C. for 20, 50 and 150 days.

6) Stability analysis of a sample of grated cheese supplemented with bacteria of the strain *Lactobacillus rhamnosus* GG (ATCC53103) at 4° C. for 20, 50 and 150 days, Table 6 and FIG. 3.

Sample 6a: Grated cheese+uncoated lyophilized bacteria ("naked" cells) of the strain *Lactobacillus rhamnosus* GG (ATCC53103) —NR.

Sample 6b: Grated cheese+bacteria of the strain *Lactobacillus rhamnosus* GG (ATCC53103). 100 grams of *Lactobacillus rhamnosus* GG (ATCC53103) at a concentration of 200 CFU/g are coated with two coating layers —R: the first coating layer consists of 50 grams of lipid (ii), whereas the second coating layer consists of 50 grams of lipid (ii)—(double coating). Ratio by weight of lyophilized bacteria:lipid (ii)+(ii)=1:1—(double coating). The coated bacteria (sample 6(b)) were mixed with a grated cheese and stored at 4° C. for 20, 50 and 150 days.

TABLE 6

| Grated cheese (shelf life 68 days) | T0 | 20 days | 50 days | 150 days |
| --- | --- | --- | --- | --- |
| | Viable cells (Billions BLN/CFUxg) | | | |
| Sample 6(b) | 1.00 | 0.86 | 0.79 | 0.600 |
| Sample 6(a) | 1.00 | 0.38 | 0.12 | 0.02 |

Figure 4:
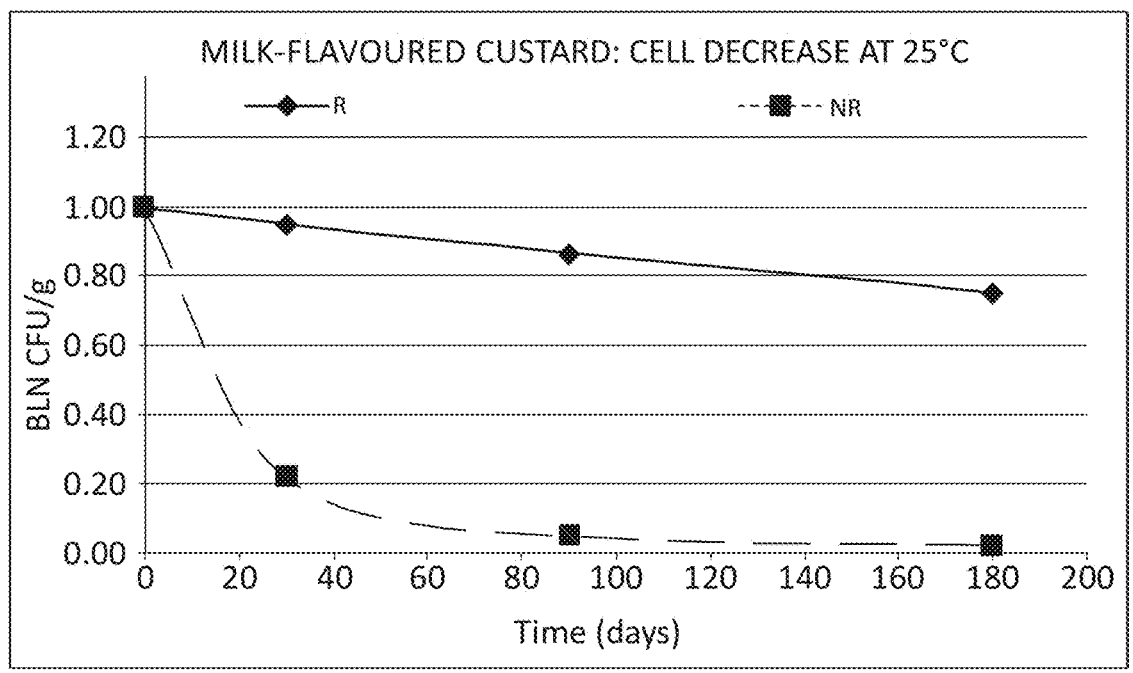
FIG. 4 shows a stability anaylsis of a sample of milk-flavoured custard for filling sweets supplemented with bacteria of the strain *Lactobacillus rhamnosus* GG (ATCC53103) at 25°C. for 30, 90 and 180 days.

7) Stability analysis of a sample of milk-flavoured custard for filling sweets supplemented with bacteria of the strain *Lactobacillus rhamnosus* GG (ATCC53103) at 25° C. for 30, 90 and 180 days, Table 7 and FIG. 4.

Sample 7a: Milk-flavoured custard for filling sweets+uncoated lyophilized bacteria ("naked" cells) of the strain *Lactobacillus rhamnosus* GG (ATCC53103) —NR.

Sample 7b: Milk-flavoured custard for filling sweets+bacteria of the strain *Lactobacillus rhamnosus* GG (ATCC53103). 100 grams of *Lactobacillus rhamnosus* GG (ATCC53103) at a concentration of 200 CFU/g are coated with two coating layers —R: the first coating layer consists of 50 grams of lipid (ii), whereas the second coating layer consists of 50 grams of lipid (ii)—(double coating). Ratio by weight of lyophilized bacteria:lipid (ii)+(ii)=1:1—(double coating). The coated bacteria (sample 7(b)) were mixed with a milk-flavoured custard for filling sweets and stored at 25° C. for 30, 90 and 180 days.

TABLE 7

| Custard for sweets | T0 | 30 days | 90 days | 180 days |
| --- | --- | --- | --- | --- |
| | Viable cells (Billions BLN/CFU/g) | | | |
| Sample 7(b) | 1.00 | 0.95 | 0.86 | 0.75 |

TABLE 7-continued

| Custard for sweets | T0 | 30 days | 90 days | 180 days |
|---|---|---|---|---|
| | | Viable cells (Billions BLN/CFU/g) | | |
| Sample 7(a) | 1.00 | 0.22 | 0.05 | 0.02 |

Figure 5:
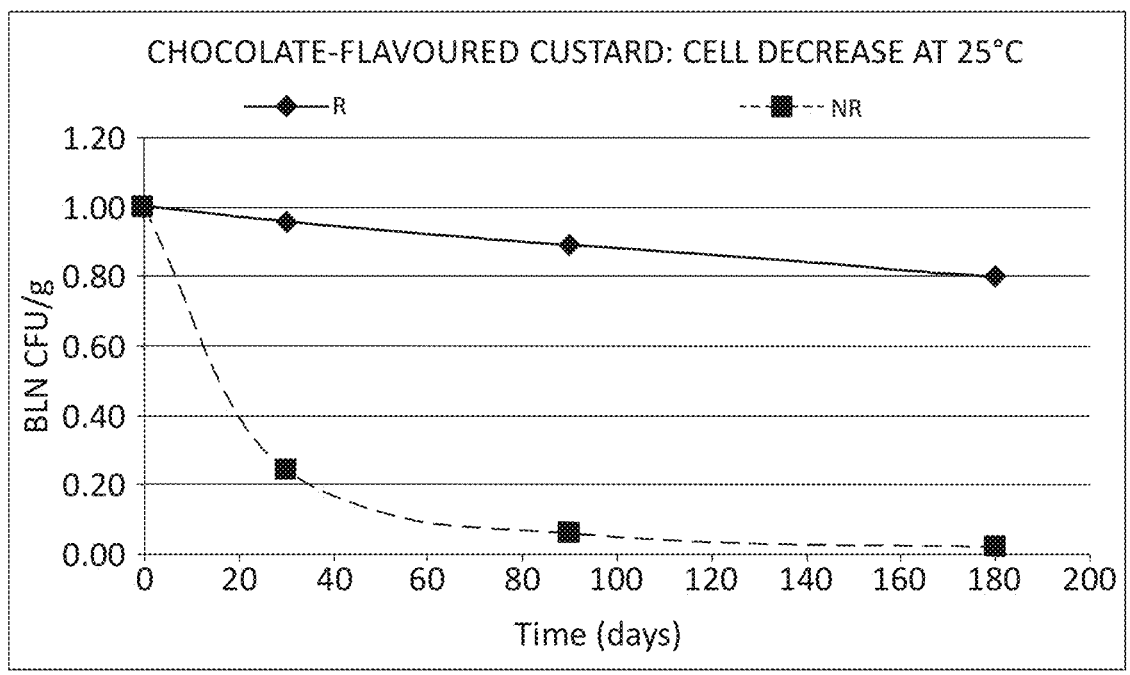
FIG. 5 shows a satbility amaylsis of a sample of chocolate-flavoured custard for filling sweets supplemented with bacteria of the strain *Lactobacillus rhamnosus* GG (ATCC53103) at 25°C. for 30, 90 and 180 days.

8) Stability analysis of a sample of chocolate-flavoured custard for filling sweets supplemented with bacteria of the strain *Lactobacillus rhamnosus* GG (ATCC53103) at 25° C. for 30, 90 and 180 days, Table 8 and FIG. 5.

Sample 8a: Chocolate-flavoured custard for filling sweets+uncoated lyophilized bacteria ("naked" cells) of the strain *Lactobacillus rhamnosus* GG (ATCC53103) —NR.

Sample 8b: Milk-flavoured custard for filling sweets+ bacteria of the strain *Lactobacillus rhamnosus* GG (ATCC53103). 100 grams of *Lactobacillus rhamnosus* GG (ATCC53103) at a concentration of 200 CFU/g are coated with two coating layers —R: the first coating layer consists of 50 grams of lipid (ii), whereas the second coating layer consists of 50 grams of lipid (ii)—(double coating). Ratio by weight of lyophilized bacteria:lipid (ii)+(ii)=1:1—(double coating). The coated bacteria (sample 8(b)) were mixed with a chocolate-flavoured custard for filling sweets and stored at 25° C. per 30, 90 and 180 days.

TABLE 8

| Custard for sweets | T0 | 30 days | 90 days | 180 days |
|---|---|---|---|---|
| | | Viable cells (Billions BLN/CFUxg) | | |
| Sample 8(b) | 1.00 | 0.96 | 0.89 | 0.80 |
| Sample 8(a) | 1.00 | 0.24 | 0.06 | 0.02 |

Figure 6:
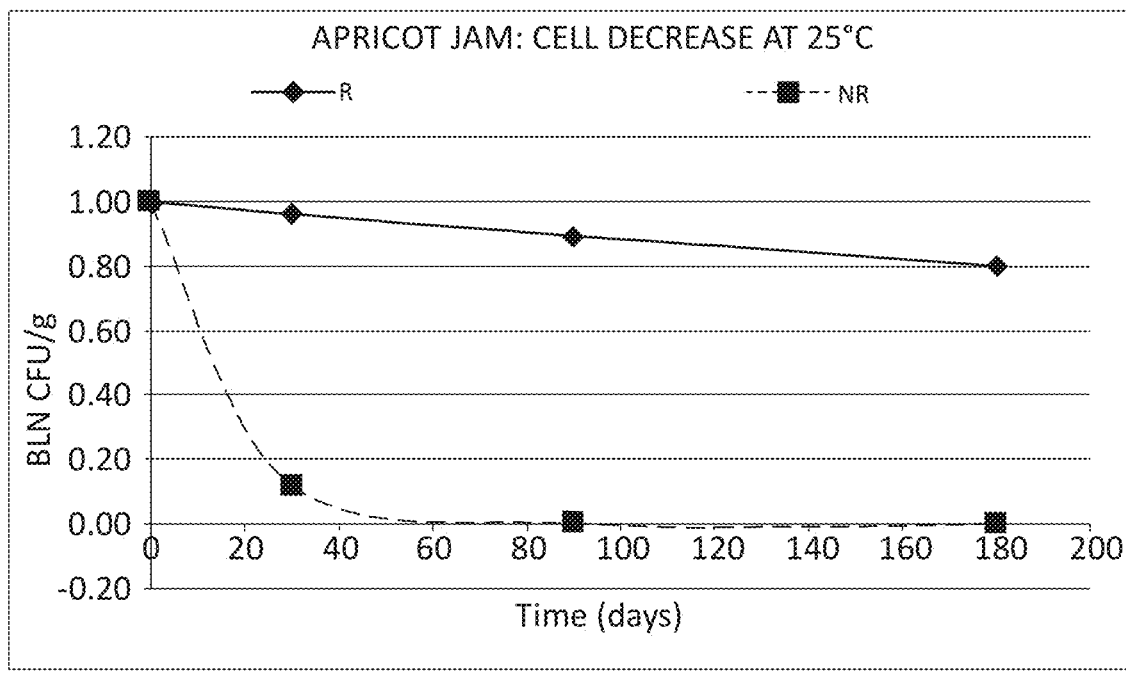
FIG. 6 shows a stability anaylsis of a sample of apricot-flavoured jam supplemented with bacteria of the strain *Lactobacillus rhamnosus* GG (ATCC53103) at 25°C. for 30, 90 and 180 days.

9) Stability analysis of a sample of apricot-flavoured jam supplemented with bacteria of the strain *Lactobacillus rhamnosus* GG (ATCC53103) at 25° C. for 30, 90 and 180 days, Table 9 and FIG. 6.

Sample 9a: Apricot-flavoured jam+uncoated lyophilized bacteria ("naked" cells) of the strain *Lactobacillus rhamnosus* GG (ATCC53103) —NR.

Sample 9b: Apricot-flavoured jam+bacteria of the strain *Lactobacillus rhamnosus* GG (ATCC53103). 100 grams of *Lactobacillus rhamnosus* GG (ATCC53103) at a concentration of 200 CFU/g are coated with two coating layers —R: the first coating layer consists of 50 grams of lipid (i), whereas the second coating layer consists of 50 grams of lipid (i)—(double coating). Ratio by weight of lyophilized bacteria:lipid (i)+(i)=1:1—(double coating). The coated bacteria (sample 9(b)) were mixed with an apricot-flavoured jam and stored at 25° C. for 30, 90 and 180 days.

TABLE 9

| Apricot jam | T0 | 30 days | 90 days | 180 days |
|---|---|---|---|---|
| | | Viable cells (Billions BLN/CFUxg) | | |
| Sample 9(b) | 1.00 | 0.96 | 0.89 | 0.800 |
| Sample 9(a) | 1.00 | 0.12 | 0.00030 | 0.000002 |

In Tables 10, 11, 12 and 13, the following expressions are used:
T=Total
R=Coated
NR=Uncoated
Days=number of days
BLN=Billion
CFU=Colony forming units
LGG *Lactobacillus rhamnosus* GG (ATCC53103)
BR03 *Bifidobacterium breve* BR03 (DSM16604)
BS01 *Bifidobacterium lactis* BS01 (LMG P-21384)
LR04 *Lactobacillus casei* ssp. *rhamnosus* LR04 (DSM 16605)
LR06 *Lactobacillus rahmnosus* LR06 (DSM 21981)
LA02 *Lactobacillus acidophilus* LA02 (LMG P-21382)
LP01 *Lactobacillus plantarum* LP 01 (LMG P-21021)

TABLE 10

Survival analysis of coated bacteria (R) in contact with toxic elements.

Viable cells MLD/UFC/g

Evaluation of toxic element

| | Time zero | | | Orange flavour | | | | | | Copper sulphate | | |
|---|---|---|---|---|---|---|---|---|---|---|---|---|
| Coated Bacteria | T | R | NR | T | R | NR | T | R | NR | T | R | NR |
| | MLD/g | | | MLD/g | | | % mortality | | | MLD/g | | |
| LGG | 110 | 92 | 18 | 91 | 90.46 | 0.54 | 17.3 | 1.7 | 97.0 | 89 | 88.977 | 0.023 |
| BR03 | 100 | 82 | 18 | 92 | 91.74 | 0.26 | 8.0 | −11.9 | 98.6 | 91 | 90.94 | 0.06 |
| BS01 | 105 | 87 | 18 | 90 | 89.64 | 0.36 | 14.3 | −3.0 | 98.0 | 82.3 | 82.242 | 0.058 |
| LR04 | 106 | 86 | 20 | 86 | 85.68 | 0.32 | 18.9 | 0.4 | 98.4 | 91.2 | 91.136 | 0.064 |
| LR06 | 100 | 80 | 20 | 91 | 90.54 | 0.46 | 9.0 | −13.2 | 97.7 | 94 | 93.977 | 0.023 |
| LA02 | 103 | 84.7 | 18.3 | 90 | 89.45 | 0.55 | 12.6 | −5.6 | 97.0 | 92 | 91.98 | 0.02 |
| LP01 | 112 | 93.4 | 18.6 | 88 | 87.49 | 0.51 | 21.4 | 6.3 | 97.3 | 91 | 90.981 | 0.019 |

Viable cells MLD/UFC/g
Evaluation of toxic element

| | Copper sulphate | | | Apricot jam | | | | | |
|---|---|---|---|---|---|---|---|---|---|
| Coated Bacteria | T | R | NR | T | R | NR | T | R | NR |
| | % mortality | | | MLD/g | | | % mortality | | |
| LGG | 19.1 | 3.3 | 99.9 | 89 | 88.977 | 0.023 | 19.1 | 3.3 | 99.9 |
| BR03 | 9.0 | −10.9 | 09.7 | 88 | 87.98 | 0.02 | 12.0 | −7.3 | 99.9 |

TABLE 10-continued

Survival analysis of coated bacteria (R) in contact with toxic elements.

| | | | | | | | | | |
|---|---|---|---|---|---|---|---|---|---|
| BS01 | 21.6 | 5.5 | 99.7 | 91.3 | 91.238 | 0.062 | 13.0 | −4.9 | 99.7 |
| LR04 | 14.0 | −6.0 | 99.7 | 92 | 91.96 | 0.04 | 13.2 | −6.9 | 99.8 |
| LR06 | 6.0 | −17.5 | 99.9 | 93 | 92.968 | 0.032 | 7.0 | −16.2 | 99.8 |
| LA02 | 10.7 | −8.6 | 99.9 | 91 | 90.984 | 0.016 | 11.7 | −7.4 | 99.9 |
| LP01 | 18.8 | 2.6 | 99.9 | 93 | 92.93 | 0.07 | 17.0 | 0.5 | 99.8 |

TABLE 11

Survival analysis of uncoated bacteria (NR) in contact with toxic elements.

| | Viable cells | | | | | |
|---|---|---|---|---|---|---|
| | Time zero | Orange flavour | | Copper sulphate | | Apricot jam | |
| NR | BLN/g | BLN/g | % mortality | BLN/g | % mortality | BLN/g | mortality |
| LGG | 120 | 0.3 | 99.8 | 0.02 | 99.98 | 0.09 | 99.93 |
| BR03 | 130 | 0.6 | 99.5 | 0.016 | 99.99 | 0.08 | 99.94 |
| BS01 | 100 | 0.15 | 99.9 | 0.032 | 99.97 | 0.032 | 99.97 |
| LR04 | 150 | 0.03 | 100.0 | 0.049 | 99.97 | 0.056 | 99.96 |
| LR06 | 120 | 0.2 | 99.8 | 0.032 | 99.97 | 0.023 | 99.98 |
| LA02 | 112 | 0.3 | 99.7 | 0.022 | 99.98 | 0.016 | 99.99 |
| LP01 | 116 | 0.16 | 99.9 | 0.026 | 99.98 | 0.018 | 99.98 |

TABLE 12

Survival analysis of coated bacteria (R) in contact with antibiotics: Ciprofloxacin (10 ug/ml)-A1. Erythromycin (0.5 ug/ml)-A2 and Ampicillin (1 ug/ml for *lactobacilli* and 0.5 ug/ml for *bifidobacteria*)-A3.

| | Viable cells | | | | | | | | | | | |
|---|---|---|---|---|---|---|---|---|---|---|---|---|
| | | | | Antibiotics | | | | | | | | |
| | Time zero | | | A1 (10 ug/ml) | | | | | | A2 (0.5 ug/ml) | | |
| Coated bacteria | T | R | NR | T | R | NR | T | R | NR | T | R | NR |
| | MLD/g | | | MLD/g | | | % mortality | | | MLD/g | | |
| LGG | 110 | 92 | 18 | 92 | 91.99 | 0.01 | 16.4 | 0.0 | 99.9 | 92 | 91.998 | 0.002 |
| BR03 | 100 | 82 | 18 | 89 | 88.88 | 0.12 | 11.0 | −8.4 | 99.3 | 89 | 88.81 | 0.19 |
| BS01 | 105 | 87 | 18 | 91.3 | 91.14 | 0.16 | 13.0 | −4.8 | 99.1 | 91 | 90.84 | 0.16 |
| LR04 | 106 | 86 | 20 | 86.7 | 86.58 | 0.12 | 18.2 | −0.7 | 99.4 | 93 | 92.9987 | 0.0013 |
| LR06 | 100 | 80 | 20 | 88.2 | 88.05 | 0.15 | 11.8 | −10.1 | 99.3 | 94 | 93.84 | 0.16 |
| LA02 | 103 | 84.7 | 18.3 | 89 | 88.9 | 0.1 | 13.6 | −5.0 | 99.5 | 97 | 96.89 | 0.11 |
| LP01 | 112 | 93.4 | 18.6 | 90 | 89.897 | 0.103 | 19.6 | 3.8 | 99.4 | 90 | 89.84 | 0.16 |

| | Viable cells | | | | | |
|---|---|---|---|---|---|---|
| | Antibiotics | | | | | |
| | A2 (0.5 ug/ml) | | | A3 | | |
| Coated bacteria | T | R | NR | T | R | NR |
| | % mortality | | | MLD/g | | | % mortality |
| LGG | 16.4 | 0.0 | 100.0 | 92 | 91.88 | 0.12 | 16.4 | 0.1 | 99.3 |
| BR03 | 11.0 | −8.3 | 98.9 | 86 | 85.898 | 0.102 | 14.0 | −4.8 | 99.4 |
| BS01 | 13.3 | −4.4 | 99.1 | 91 | 90.987 | 0.013 | 13.3 | −4.6 | 99.9 |
| LR04 | 12.3 | −8.1 | 100.0 | 90.3 | 90.288 | 0.012 | 14.8 | −5.0 | 99.9 |
| LR06 | 6.0 | −17.3 | 99.2 | 86.3 | 86.197 | 0.103 | 13.7 | −7.7 | 99.5 |
| LA02 | 5.8 | −14.4 | 99.4 | 89.1 | 88.994 | 0.106 | 13.5 | −5.1 | 99.4 |
| LP01 | 19.6 | 3.8 | 99.1 | 90 | 89.898 | 0.102 | 19.6 | 3.7 | 99.5 |

T = Total, R = Coated, NR = Uncoated.

TABLE 13

Survival analysis of coated lyophilized bacteria (NR) in contact with antibiotics: Ciprofloxacin (10 ug/ml)-A1. Erythromycin (0.5 ug/ml)-A2 and Ampicillin (1 ug/ml for *lactobacilli* and 0.5 ug/ml for *bifidobacteria*)-A3.

| | | Viable cells | | | | | |
|---|---|---|---|---|---|---|---|
| | Time zero | A1 (10 ug/ml) | | A2 (0.5 ug/ml) | | A3 | |
| NR | BLN/g | BLN/g | % mortality | BLN/g | % mortality | BLN/g | % mortality |
| LGG | 120 | 0.1 | 99.9 | 0.09 | 99.93 | 0.11 | 99.91 |
| BR03 | 130 | 1.02 | 99.2 | 1.3 | 99.00 | 0.103 | 99.92 |
| BS01 | 100 | 0.102 | 99.9 | 1.23 | 98.77 | 0.111 | 99.89 |
| LR04 | 150 | 0.12 | 99.9 | 0.01 | 99.99 | 0.023 | 99.98 |
| LR06 | 120 | 0.13 | 99.9 | 0.13 | 99.89 | 0.106 | 99.91 |
| LA02 | 112 | 0.2 | 99.8 | 0.12 | 99.89 | 0.16 | 99.86 |
| LP01 | 116 | 0.1 | 99.9 | 0.16 | 99.86 | 0.12 | 99.90 |

T = Total, R = Coated, NR = Uncoated.

TABLE A

| No. | Name | Comm name | Deposit institution | Deposit number | Deposit number | Owner |
|---|---|---|---|---|---|---|
| 1 | *Lactobacillus casei* | LF1i | CNCM I.P. | I-785 | 21.07.1988 | Anidral Srl |
| 2 | *Lactobacillus gasseri* | LF2i | CNCM I.P. | I-786 | 21.07.1988 | Anidral Srl |
| 3 | *Lactobacillus crispatus* | LF3i | CNCM I.P. | I-787 | 21.07.1988 | Anidral Srl |
| 4 | *Lactobacillus fermentum* | LF4i | CNCM I.P. | I-788 | 21.07.1988 | Anidral Srl |
| 5 | *Lactobacillus fermentum* | LF5 | CNCM I.P. | I-789 | 21.07.1988 | Anidral Srl |
| 6 | *Lactobacillus casei* ssp. *pseudoplantarum* | LFH the | CNCM I.P. | I-790 | 21.07.1988 | Anidral Srl |
| 7 | *Streptococcus thermophilus* B39 | | BCCM LMG | LMG P-18383 | 5.05.1998 | Anidral Srl |
| 8 | *Streptococcus thermophilus* T003 | | BCCM LMG | LMG P-18384 | 5.05.1998 | Anidral Srl |
| 9 | Lactobacillus pentosus 9/lei | | BCCM LMG | LMG P-21019 | 16.10.2001 | Mofin Srl |
| 10 | *Lactobacillus plantarum* 776/1 bi | LP 02 | BCCM LMG | LMG P-21020 | 16.10.2001 | Mofin Srl |
| 11 | *Lactobacillus plantarum* 476LL 20 bi | LP 01 | BCCM LMG | LMG P-21021 | 16.10.2001 | Mofin Srl |
| 12 | *Lactobacillus plantarum* PRci | | BCCM LMG | LMG P-21022 | 16.10.2001 | Mofin Srl |
| 13 | *Lactobacillus plantarum* 776/2 hi | | BCCM LMG | LMG P-21023 | 16.10.2001 | Mofin Srl |
| 14 | *Lactobacillus casei* ssp. *paracasei* 181A/3 aiai | LPC00 | BCCM LMG | LMG P-21380 | 31.01.2002 | Anidral Srl |
| 15 | *Lactobacillus* belonging to the *acidophilus* group 192A/1 aiai | LA 02 | BCCM LMG | LMG P-21381 | 31.01.2002 | Anidral Srl |
| 16 | *Bifidobacterium longum* 175A/1 aiai | | BCCM LMG | LMG P-21382 | 31.01.2002 | Anidral Srl |
| 17 | *Bifidobacterium breve* 195A/1 aici | | BCCM LMG | LMG P-21383 | 31.01.2002 | Anidral Srl |
| 18 | *Bifidobacterium lactis* 32A/3 aiai | BS 01 | BCCM LMG | LMG P-21384 | 31.01.2002 | Anidral Srl |
| 19 | *Lactobacillus plantarum* 501/2 gi | COAKTIV | BCCM LMG | LMG P-21385 | 31.01.2002 | Mofin Srl |
| 20 | *Lactococcus lactis* ssp. *lactis* 501/4 ci | | BCCM LMG | LMG P-21388 | 31.01.2002 | Mofin Srl |
| 21 | *Lactococcus lactis* ssp.*lactis* 501/4 hi | | BCCM LMG | LMG P-21387 | 15.03.2002 | Mofin Srl |
| 22 | *Lactococcus lactis* ssp.*lactis* 501/4 ci | | BCCM LMG | LMG P-21388 | 31.01.2002 | Mofin Srl |
| 23 | *Lactobacillus plantarum* 501/4 li | | BCCM LMG | LMG P-21389 | 15.03.2002 | Mofin Srl |
| 24 | *Lactobacillus acidophilus* | LA08 | BCCM LMG | LMG P-26144 | 03.11.2010 | Probiotical SpA |
| 25 | *Lactobacillus paracasei* ssp. *paracasei* | LPC 10 | BCCM LMG | LMG P-26143 | 03.11.2010 | Probiotical SpA |
| 26 | *Streptococcus thermophilus* | GB1 | DSMZ | DSM 16506 | 18.06.2004 | Anidral Srl |
| 27 | *Streptococcus thermophilus* | GB5 | DSMZ | DSM 16507 | 18.06.2004 | Anidral Srl |
| 28 | *Streptococcus thermophilus* | Y02 | DSMZ | DSM 16590 | 20.07.2004 | Anidral Srl |
| 29 | *Streptococcus thermophilus* | Y03 | DSMZ | DSM 16591 | 20.07.2004 | Anidral Srl |
| 30 | *Streptococcus thermophilus* | Y04 | DSMZ | DSM 16592 | 20.07.2004 | Anidral Srl |
| 31 | *Streptococcus thermophilus* | YO5 | DSMZ | DSM 16593 | 20.07.2004 | Anidral Srl |

TABLE A-continued

| No. | Name | Comm name | Deposit institution | Deposit number | Deposit number | Owner |
|---|---|---|---|---|---|---|
| 32 = 56 | *Bifidobacterium adolescentis* | BA 03 | DSMZ | DSM 16594 | 21.07.2004 | Anidral Srl |
| 33 | *Bifidobacterium adolescentis* | BA 04 | DSMZ | DSM 16595 | 21.07.2004 | Anidral Srl |
| 34 | *Bifidobacterium breve* | BR 04 | DSMZ | DSM 16596 | 21.07.2004 | Anidral Srl |
| 35 | *Bifidobacterium pseudocatenulatum* | BP 01 | DSMZ | DSM 16597 | 21.07.2004 | Anidral Srl |
| 36 | *Bifidobacterium pseudocatenulatum* | BP 02 | DSMZ | DSM 16598 | 21.07.2004 | Anidral Srl |
| 37 | *Bifidobacterium longum* | BL 03 | DSMZ | DSM 16603 | 20.07.2004 | Anidral Srl |
| 38 | *Bifidobacterium breve* | BR 03 | DSMZ | DSM 16604 | 20.07.2004 | Anidral Srl |
| 39 | *Lactobacillus casei ssp. rhamnosus* | LR 04 | DSMZ | DSM 16605 | 20.07.2004 | Anidral Srl |
| 40 | *Lactobacillus delbrueckii ssp. bulgaricus* | LDB 01 | DSMZ | DSM 16606 | 20.07.2004 | Anidral Srl |
| 41 | *Lactobacillus delbrueckii ssp.bulgaricus* | LDB 02 | DSMZ | DSM 16607 | 20.07.2004 | Anidral Srl |
| 42 | *Staphylococcus xylosus* | SX 01 | DSMZ | DSM 17102 | 01.02.2005 | Anidral Srl |
| 43 = 57 | *Bifidobacterium adolescentis* | BA 02 | DSMZ | DSM 17103 | 01.02.2005 | Anidral Srl |
| 44 | *Lactobacillus plantarum* | LP 07 | DSMZ | DSM 17104 | 01.02.2005 | Anidral Srl |
| 45 | *Streptococcus thermophilus* | YO8 | DSMZ | DSM 17843 | 21.12.2005 | Anidral Srl |
| 46 | *Streptococcus thermophilus* | YO9 | DSMZ | DSM 17844 | 21.12.2005 | Anidral Srl |
| 47 | *Streptococcus thermophilus* | YO100 | DSMZ | DSM 17845 | 21.12.2005 | Anidral Srl |
| 48 | *Lactobacillus fermentum* | LF06 | DSMZ | DSM 18295 | 24.05.2006 | Anidral Srl |
| 49 | *Lactobacillus fermentum* | LF07 | DSMZ | DSM 18296 | 24.05.2006 | Anidral Srl |
| 50 | *Lactobacillus fermentum* | LF08 | DSMZ | DSM 18297 | 24.05.2006 | Anidral Srl |
| 51 | *Lactobacillus fermentum* | LF09 | DSMZ | DSM 18298 | 24.05.2006 | Anidral Srl |
| 52 | *Lactobacillus gasseri* | LGS01 | DSMZ | DSM 18299 | 24.05.2006 | Anidral Srl |
| 53 | *Lactobacillus gasseri* | LGS02 | DSMZ | DSM 18300 | 24.05.2006 | Anidral Srl |
| 54 | *Lactobacillus gasseri* | LGS03 | DSMZ | DSM 18301 | 24.05.2006 | Anidral Srl |
| 55 | *Lactobacillus gasseri* | LGS04 | DSMZ | DSM 18302 | 24.05.2006 | Anidral Srl |
| 56 = 32 | *Bifidobacterium adolescentis* EI-3 *Bifidobacterium catenulatum sp./pseudocatenulatum* EI-3I, ID 09-255 | BA 03 | DSMZ | DSM 18350 | 15.06.2006 | Anidral Srl |
| 57 = 43 | *Bifidobacterium adolescentis* EI-15 | BA 02 | DSMZ | DSM 18351 | 15.06.2006 | Anidral Srl |
| 58 | *Bifidobacterium adolescentis* EI-18 *Bifidobacterium animalis* subsp. *lactis* EI-18, ID 09-256 | BA 05 | DSMZ | DSM 18352 | 15.06.2006 | Anidral Srl |
| 59 | *Bifidobacterium catenulatum* EI-20 | BC 01 | DSMZ | DSM 18353 | 15.06.2006 | Anidral Srl |
| 60 | *Streptococcus thermophilus* FRai | MO1 | DSMZ | DSM 18613 | 13.09.2006 | Mofin Srl |
| 61 | *Streptococcus thermophilus* LB2bi | MO2 | DSMZ | DSM 18614 | 13.09.2006 | Mofin Srl |
| 62 | *Streptococcus thermophilus* LRci | MO3 | DSMZ | DSM 18615 | 13.09.2006 | Mofin Srl |
| 63 | *Streptococcus thermophilus* FP4 | MO4 | DSMZ | DSM 18616 | 13.09.2006 | Mofin Srl |
| 64 | *Streptococcus thermophilus* ZZ5F8 | MO5 | DSMZ | DSM 18617 | 13.09.2006 | Mofin Srl |
| 65 | *Streptococcus thermophilus* TEO4 | MO6 | DSMZ | DSM 18618 | 13.09.2006 | Mofin Srl |
| 66 | *Streptococcus thermophilus* Slci | MO7 | DSMZ | DSM 18619 | 13.09.2006 | Mofin Srl |
| 67 | *Streptococcus thermophilus* 641bi | MO8 | DSMZ | DSM 18620 | 13.09.2006 | Mofin Srl |
| 68 | *Streptococcus thermophilus* 277A/1ai | MO9 | DSMZ | DSM 18621 | 13.09.2006 | Mofin Srl |
| 69 | *Streptococcus thermophilus* 277A/2ai | MO10 | DSMZ | DSM 18622 | 13.09.2006 | Mofin Srl |
| 70 | *Streptococcus thermophilus* IDC11 | MO11 | DSMZ | DSM 18623 | 13.09.2006 | Mofin Srl |
| 71 | *Streptococcus thermophilus* ML3di | MO14 | DSMZ | DSM 18624 | 13.09.2006 | Mofin Srl |
| 72 | *Streptococcus thermophilus* TEO3 | MO15 | DSMZ | DSM 18625 | 13.09.2006 | Mofin Srl |

TABLE A-continued

| No. | Name | Comm name | Deposit institution | Deposit number | Deposit number | Owner |
|---|---|---|---|---|---|---|
| 73 | *Streptococcus thermophilus* G62 | GG1 | DSMZ | DSM 19057 | 21.02.2007 | Mofin Srl |
| 74 | *Streptococcus thermophilus* G1192 | GG2 | DSMZ | DSM 19058 | 21.02.2007 | Mofin Srl |
| 75 | *Streptococcus thermophilus* GB18 | GG3 MO2 | DSMZ | DSM 19059 | 21.02.2007 | Mofin Srl |
| 76 | *Streptococcus thermophilus* CCR21 | GG4 | DSMZ | DSM 19060 | 21.02.2007 | Mofin Srl |
| 77 | *Streptococcus thermophilus* G92 | GG5 | DSMZ | DSM 19061 | 21.02.2007 | Mofin Srl |
| 78 | *Streptococcus thermophilus* G69 | GG6 | DSMZ | DSM 19062 | 21.02.2007 | Mofin Srl |
| 79 | *Streptococcus thermophilus* | YO 10 | DSMZ | DSM 19063 | 21.02.2007 | Anidral Srl |
| 80 | *Streptococcus thermophilus* | YO 11 | DSMZ | DSM 19064 | 21.02.2007 | Anidral Srl |
| 81 | *Streptococcus thermophilus* | YO 12 | DSMZ | DSM 19065 | 21.02.2007 | Anidral Srl |
| 82 | *Streptococcus thermophilus* | YO 13 | DSMZ | DSM 19066 | 21.02.2007 | Anidral Srl |
| 83 | *Weissella* ssp. WSP 01 | EX | DSMZ | DSM 19067 | 21.02.2007 | Anidral Srl |
| 84 | *Weissella* ssp. WSP 02 | EX | DSMZ | DSM 19068 | 21.02.2007 | Anidral Srl |
| 85 | *Lactobacillus* ssp. WSP 03 | EX | DSMZ | DSM 19069 | 21.02.2007 | Anidral Srl |
| 86 | *Lactobacillus plantarum* LP 09 | OY | DSMZ | DSM 19070 | 21.02.2007 | Anidral Srl |
| 87 | *Lactobacillus plantarum* LP 10 | OY | DSMZ | DSM 19071 | 21.02.2007 | Anidral Srl |
| 88 | *Lactococcus lactis* | NS 01 | DSMZ | DSM 19072 | 21.02.2007 | Anidral Srl |
| 89 | *Lactobacillus fermentum* | LF 10 | DSMZ | DSM 19187 | 20.03.2007 | Anidral Srl |
| 90 | *Lactobacillus fermentum* | LF 11 | DSMZ | DSM 19188 | 20.03.2007 | Anidral Srl |
| 91 | *Lactobacillus casei* ssp. *rhamnosus* | LR05 | DSMZ | DSM 19739 | 27.09.2007 | Anidral Srl |
| 92 | *Bifidobacterium bifidum* | BB01 | DSMZ | DSM 19818 | 30.10.2007 | Anidral Srl |
| 93 | *Lactobacillus delbrueckii* subsp. *bulgaricus* LD 01 | Lb | DSMZ | DSM 19948 | 28.11.2007 | Anidral Srl |
| 94 | *Lactobacillus delbrueckii* subsp.*bulgaricus* LD 02 | Lb | DSMZ | DSM 19949 | 28.11.2007 | Anidral Srl |
| 95 | *Lactobacillus delbrueckii* subsp.*bulgaricus* LD 03 | Lb | DSMZ | DSM 19950 | 28.11.2007 | Anidral Srl |
| 96 | *Lactobacillus delbrueckii* subsp. *bulgaricus* LD 04 | Lb | DSMZ | DSM 19951 | 28.11.2007 | Anidral Srl |
| 97 | *Lactobacillus delbrueckii* subsp.*bulgaricus* LD 05 | Lb | DSMZ | DSM 19952 | 28.11.2007 | Anidral Srl |
| 98 | *Bifidobacterium pseudocatenulatum* | B660 | DSMZ | DSM 21444 | 13.05.2008 | Probiotical SpA |
| 99 | *Lactobacillus acidophilus* | LA02 | DSMZ | DSM 21717 | 06.08.2008 | Probiotical SpA |
| 100 | *Lactobacillus paracasei* | LPC 08 | DSMZ | DSM 21718 | 06.08.2008 | Probiotical SpA |
| 101 | *Lactobacillus pentosus* | LPS 01 | DSMZ | DSM 21980 | 14.11.2008 | Probiotical SpA |
| 102 | *Lactobacillus rahmnosus* | LR 06 | DSMZ | DSM 21981 | 14.11.2008 | Probiotical SpA |
| 103 | *Lactobacillus delbrueckii* ssp.*delbrueckii* | DSMZ 20074 | DSMZ | DSM 22106 | 10.12.2008 | Probiotical SpA |
| 104 | *Lactobacillus plantarum* | LP1 | DSMZ | DSM 22107 | 10.12.2008 | Probiotical SpA |
| 105 | *Lactobacillus salivarius* | LS01 | DSMZ | DSM 22775 | 23.07.2009 | Probiotical SpA |
| 106 | *Lactobacillus salivarius* | LS03 | DSMZ | DSM 22776 | 23.07.2009 | Probiotical SpA |
| 107 | *Bifidobacterium bifidum* | BB01 | DSMZ | DSM 22892 | 28.08.2009 | Probiotical SpA |
| 108 | *Bifidobacterium bifidum* | | DSMZ | DSM 22893 | 28.08.2009 | Probiotical SpA |
| 109 | *Bifidobacterium bifidum* | BB03 | DSMZ | DSM 22894 | 28.08.2009 | Probiotical SpA |
| 110 | *Bifidobacterium lactis* | BS05 | DSMZ | DSM 23032 | 13.10.2009 | Probiotical SpA |
| 111 | *Lactobacillus acidophilus* | LA 06 | DSMZ | DSM 23033 | 13.10.2009 | Probiotical SpA |
| 112 | *Lactobacillus brevis* | LBR01 | DSMZ | DSM 23034 | 13.10.2009 | Probiotical SpA |
| 113 | *Bifidobacterium animalis* ssp. *lactis* | BS06 | DSMZ | DSM 23224 | 12.01.2010 | Probiotical SpA |
| 114 | *Bifidobacterium longum* | BL04 | DSMZ | DSM 23233 | 12.01.2010 | Probiotical SpA |
| 115 | *Bifidobacterium longum* | BL05 | DSMZ | DSM 23234 | 12.01.2010 | Probiotical SpA |
| 116 | *Bifidobacterium bifidum* | MB 109 | DSMZ | DSM 23731 | 29.06.2010 | Probiotical SpA |
| 117 | *Bifidobacterium breve* | MB 113 | DSMZ | DSM 23732 | 29.06.2010 | Probiotical SpA |
| 118 | *Bifidobacterium lactis* | MB 2409 | DSMZ | DSM 23733 | 29.06.2010 | Probiotical SpA |
| 119 | *Lactobacillus reuteri* | LRE01 | DSMZ | DSM 23877 | 05.08.2010 | Probiotical SpA |
| 120 | *Lactobacillus reuteri* | LRE02 | DSMZ | DSM 23878 | 05.08.2010 | Probiotical SpA |
| 121 | *Lactobacillus reuteri* | LRE03 | DSMZ | DSM 23879 | 05.08.2010 | Probiotical SpA |
| 122 | *Lactobacillus reuteri* | LRE04 | DSMZ | DSM 23880 | 05.08.2010 | Probiotical SpA |
| 123 | *Lactobacillus paracasei* ssp. *paracasei* | LPC09 | DSMZ | DSM 24243 | 23.11.2010 | Probiotical SpA |
| 124 | *Lactobacillus acidophilus* | LA 07 | DSMZ | DSM 24303 | 23.11.2010 | Probiotical SpA |
| 125 | *Bifidobacterium bifidum* | BB04 | DSMZ | DSM 24437 | 04.01.2011 | Probiotical SpA |
| 126 | *Lactobacillus crispatus* | CRL 1251 | DSMZ | DSM 24438 | 04.01.2011 | Probiotical SpA |
| 127 | *Lactobacillus crispatus* | CRL 1266 | DSMZ | DSM 24439 | 04.01.2011 | Probiotical SpA |
| 128 | *Lactobacillus paracasei* | CRL 1289 | DSMZ | DSM 24440 | 04.01.2011 | Probiotical SpA |

TABLE A-continued

| No. | Name | Comm name | Deposit institution | Deposit number | Deposit number | Owner |
|---|---|---|---|---|---|---|
| 129 | Lactobacillus salivarius | CRL 1328 | DSMZ | DSM 24441 | 04.01.2011 | Probiotical SpA |
| 130 | Lactobacillus gasseri | CRL 1259 | DSMZ | DSM 24512 | 25.01.2011 | Probiotical SpA |
| 131 | Lactobacillus acidophilus | CRL 1294 | DSMZ | DSM 24513 | 25.01.2011 | Probiotical SpA |
| 132 | Lactobacillus salivarius | LS04 | DSMZ | DSM 24618 | 02.03.2011 | Probiotical SpA |
| 133 | Lactobacillus crispatus | LCR01 | DSMZ | DSM 24619 | 02.03.2011 | Probiotical SpA |
| 134 | Lactobacillus crispatus | LCR02 | DSMZ | DSM 24620 | 02.03.2011 | Probiotical SpA |
| 135 | Lacotbacillus acidophilus | LA09 | DSMZ | DSM 24621 | 02.03.2011 | Probiotical SpA |
| 136 | Lactobacillus gasseri | LGS05 | DSMZ | DSM 24622 | 02.03.2011 | Probiotical SpA |
| 137 | Lactobacillus paracasei | LPC11 | DSMZ | DSM 24623 | 02.03.2011 | Probiotical SpA |
| 138 | Bifidobacterium injantis | BI 02 | DSMZ | DSM 24687 | 29.03.2011 | Probiotical SpA |
| 139 | Bifidobacterium bifidum | BB 06 | DSMZ | DSM 24688 | 29.03.2011 | Probiotical SpA |
| 140 | Bifidobacterium longum | BL 06 | DSMZ | DSM 24689 | 29.03.2011 | Probiotical SpA |
| 141 | Bifidobacterium lactis | BS 07 | DSMZ | DSM 24690 | 29.03.2011 | Probiotical SpA |
| 142 | Bifidobacterium longum | PCB133 | DSMZ | DSM 24691 | 29.03.2011 | Probiotical SpA |
| 143 | Bifidobacterium breve | B632 | DSMZ | DSM 24706 | 07.04.2011 | Probiotical SpA |
| 144 | Bifidobacterium breve | B2274 | DSMZ | DSM 24707 | 07.04.2011 | Probiotical SpA |
| 145 | Bifidobacterium breve | B7840 | DSMZ | DSM 24708 | 07.04.2011 | Probiotical SpA |
| 146 | Bifidobacterium longum | B1975 | DSMZ | DSM 24709 | 07.04.2011 | Probiotical SpA |
| 147 | Lactobacillus salivarius | DLV1 | DSMZ | DSM 25138 | 02.09.2011 | Probiotical SpA |
| 148 | Lactobacillus reuteri | LRE05 | DSMZ | DSM 25139 | 02.09.2011 | Probiotical SpA |
| 149 | Lactobacillus reuteri | LRE06 | DSMZ | DSM 25140 | 02.09.2011 | Probiotical SpA |
| 150 | Lactobacillus reuteri | RC 14 | DSMZ | DSM 25141 | 02.09.2011 | Probiotical SpA |
| 151 | Streptococcus thermophilus | ST 10 | DSMZ | DSM 25246 | 19.09.2011 | Probiotical SpA |
| 152 | Streptococcus thermophilus | ST 11 | DSMZ | DSM 25247 | 19.09.2011 | Probiotical SpA |
| 153 | Streptococcus thermophilus | ST 12 | DSMZ | DSM 25282 | 20.10.2011 | Probiotical SpA |
| 154 | Lactobacillus salivarius | DLV8 | DSMZ | DSM 25545 | 12.01.2012 | Probiotical SpA |
| 155 | Bifidobacterium longum | DLBL 07 | DSMZ | DSM 25669 | 16.02.2012 | Probiotical SpA |
| 156 | Bifidobacterium longum | DLBL 08 | DSMZ | DSM 25670 | 16.02.2012 | Probiotical SpA |
| 157 | Bifidobacterium longum | DLBL 09 | DSMZ | DSM 25671 | 16.02.2012 | Probiotical SpA |
| 158 | Bifidobacterium longum | DLBL 10 | DSMZ | DSM 25672 | 16.02.2012 | Probiotical SpA |
| 159 | Bifidobacterium longum | DLBL 11 | DSMZ | DSM 25673 | 16.02.2012 | Probiotical SpA |
| 160 | Bifidobacterium longum | DLBL 12 | DSMZ | DSM 25674 | 16.02.2012 | Probiotical SpA |
| 161 | Bifidobacterium longum | DLBL13 | DSMZ | DSM 25675 | 16.02.2012 | Probiotical SpA |
| 162 | Bifidobacterium longum | DLBL 14 | DSMZ | DSM 25676 | 16.02.2012 | Probiotical SpA |
| 163 | Bifidobacterium longum | DLBL 15 | DSMZ | DSM 25677 | 16.02.2012 | Probiotical SpA |
| 164 | Bifidobacterium longum | DLBL 16 | DSMZ | DSM 25678 | 16.02.2012 | Probiotical SpA |
| 165 | Bifidobacterium longum | DLBL 17 | DSMZ | DSM 25679 | 16.02.2012 | Probiotical SpA |
| 166 | Lactobacillus johnsonii | DLLJO 01 | DSMZ | DSM 25680 | 16.02.2012 | Probiotical SpA |
| 167 | Lactobacillus rhamnosus | DLLR 07 | DSMZ | DSM 25681 | 16.02.2012 | Probiotical SpA |
| 168 | Lactobacillus rhamnosus | DLLR 08 | DSMZ | DSM 25682 | 16.02.2012 | Probiotical SpA |
| 169 | Lactobacillus reuteri | DLLRE 07 | DSMZ | DSM 25683 | 16.02.2012 | Probiotical SpA |
| 170 | Lactobacillus reuteri | DLLRE 08 | DSMZ | DSM 25684 | 16.02.2012 | Probiotical SpA |
| 171 | Lactobacillus reuteri | DLLRE 09 | DSMZ | DSM 25685 | 16.02.2012 | Probiotical SpA |
| 172 | Bifidobacterium longum | DLBL 18 | DSMZ | DSM 25708 | 24.02.2012 | Probiotical SpA |
| 173 | Bifidobacterium infantis | BI 03 | DSMZ | DSM 25709 | 24.02.2012 | Probiotical SpA |
| 174 | Lactobacillus plantarum | LP 09 | DSMZ | DSM 25710 | 24.02.2012 | Probiotical SpA |
| 175 | Bifidobacterium longum | DLBL 19 | DSMZ | DSM 25717 | 01.03.2012 | Probiotical SpA |
| 176 | Bifidobacterium longum | DLBL 20 | DSMZ | DSM 25718 | 01.03.2012 | Probiotical SpA |
| 177 | Lactobacillus salivarius | LS 05 | DSMZ | DSM 26036 | 06.06.2012 | Probiotical SpA |
| 178 | Lactobacillus salivarius | LS 06 | DSMZ | DSM 26037 | 06.06.2012 | Probiotical SpA |
| 179 | Lactobacillus pentosus | LPS 02 | DSMZ | DSM 26038 | 06.06.2012 | Probiotical SpA |
| 180 | Bifidobacterium pseudolongum ssp. globosum | BPS 01 | DSMZ | DSM 26456 | 02.10.2012 | Probiotical SpA |

The present invention relates to the following points:

1. Bacteria coated with a coating comprising lipids of vegetable origin characterized in that said coating is a multilayer coating formed of a number of coating layers n comprised from 2 to 10, and in that:
   when n=2, a first coating layer, formed on the outer surface of the bacteria, and a second coating layer, formed on the outer surface of said first coating layer, said first and second layer comprise or, alternatively, consist of a lipid of vegetable origin which is the same between them, or
   when n=2, a first coating layer, formed on the outer surface of the bacteria, and a second coating layer, formed on the outer surface of said first coating layer, said first and second layer comprise or, alternatively, consist of a lipid of vegetable origin represented by a glyceryl dipalmitostearate E471-lipid (i), said lipid (i) being present in said first layer or, alternatively, in said second layer, but not in both layers, and in that:
   when n is comprised from 3 to 10, the coating layers comprise or, alternatively, consist of at least one lipid of vegetable origin.

2. The bacteria according to point 1, wherein the lipids are selected from the group comprising the saturated vegetable fats having a melting point comprised from 35° C. to 85° C., preferably comprised from 45 to 70° C.

3. The bacteria according to point 1 or 2, wherein the lipids are selected from the group comprising mono- and di-glycerides of saturated fatty acids, polyglycerols esterified with saturated fatty acids and free saturated fatty acids; preferably they are selected from the group comprising a glyceryl dipalmitostearate E471-lipid (i), a polyglyceryl-6-distearate E475-lipid (ii), a mixture of esters of glycerol and fatty acids C16-C18-lipid (iii) and a hydrogenated vegetable fat of non-lauric origin-lipid (iv).

4. The bacteria according to any one of points 1-3, wherein when n is 2, a first and second coating layer comprise or, alternatively, consist of at least one lipid of vegetable origin which is the same between them and selected from the group comprising or, alternatively, consisting of lipids (i), (ii), (iii) and (iv); preferably said first coating layer comprising or, alternatively, consisting of lipid (i) and said second coating layer comprising or, alternatively, consisting of lipid (i).

5. The bacteria according to any one of points 1-3, wherein when n is 2, a first and second coating layer comprise or, alternatively, consist of at least one lipid of vegetable origin which is the same between them and selected from the group comprising or, alternatively, consisting of lipids (i), (ii), (iii) and (iv); preferably said first coating layer comprising or, alternatively, consisting of the lipid (ii) and said second coating layer comprising or, alternatively, consisting of lipid (ii).

6. The bacteria according to any one of points 1-3, wherein when n is 2, a first coating layer comprises or, alternatively, consists of lipid (i) and a second coating layer comprises or, alternatively, consists of lipid (ii), (iii) and (iv).

7. The bacteria according to any one of points 1-3, wherein when n is 2, a first coating layer comprises or, alternatively, consists of lipid (ii) and a second coating layer comprises or, alternatively, consists of lipid (i), (iii) and (iv).

8. The bacteria according to any one of points 1-3, wherein when n is 3 a first and second coating layer comprise or, alternatively, consist of lipid (i) and a third coating layer comprises or, alternatively, consists of lipid (ii), (iii) and (iv) or, alternatively, a first and second coating layer comprise or, alternatively, consist of lipid (ii) and a third coating layer comprises or, alternatively, consists of lipid (i), (iii) and (iv).

9. The bacteria according to any one of points 1-8, wherein said coated bacteria have a concentration comprised from $1\times10^6$ to $1\times10^{11}$ CFU/g, preferably $1\times10^7$ to $1\times10^{10}$ CFU/g, even more preferably $1\times10^8$ to $1\times10^{10}$ CFU/g.

10. A food product or a medical device or a supplement product comprising the coated bacteria according to any one of points 1-9.

11. The food product according to point 10, wherein the coated bacteria, preferably at a concentration comprised from $1\times10^6$ to $1\times10^{11}$ CFU/g or $1\times10^7$ to $1\times10^{10}$ CFU/g or $1\times10^8$ to $1\times10^{10}$ CFU/g, are introduced into a food selected from the group comprising:

powdered milk, in a quantity comprised from 0.1 to 20% by weight, preferably 0.5 to 10% by weight, even more preferably 1 to 5% by weight, relative to the weight of the food product;

fresh milk, in a quantity comprised from 0.1 to 20% by weight, preferably 0.5 to 10% by weight, even more preferably 1 to 5% by weight, relative to the weight of the food product;

butter or margarine, in a quantity comprised from 0.1 to 20% by weight, preferably 0.5 to 10% by weight, even more preferably 1 to 5% by weight, relative to the weight of the food product;

cream or yogurt, in a quantity comprised from 0.1 to 20% by weight, preferably 0.5 to 10% by weight, even more preferably 1 to 5% by weight, relative to the weight of the food product;

grated cheese, in a quantity comprised from 0.1 to 20% by weight, preferably 0.5 to 10% by weight, even more preferably 1 to 5% by weight, relative to the weight of the food product;

milk-flavoured custard for filling sweets, in a quantity comprised from 0.1 to 20% by weight, preferably 0.5 to 10% by weight, even more preferably 1 to 5% by weight, relative to the weight of the food product;

chocolate-flavoured custard for filling sweets, in a quantity comprised from 0.1 to 20% by weight, preferably 0.5 to 10% by weight, even more preferably 1 to 5% by weight, relative to the weight of the food product;

apricot-flavoured jam, in a quantity comprised from 0.1 to 20% by weight, preferably 0.5 to 10% by weight, even more preferably 1 to 5% by weight, relative to the weight of the food product.

12. A pharmaceutical composition comprising the coated bacteria according to any one of points 1-9 and at least one pharmaceutical active ingredient with antibiotic activity; preferably an antibiotic selected from the group comprising ciprofloxacin, erythromycin and ampicillin.

The invention claimed is:

1. Bacteria coated with a coating comprising lipids of vegetable origin, wherein said coating is a multilayer coating comprising at least a first coating layer and a second coating layer, the first coating layer and the second coating layer made from the same coating material, wherein:

the first coating layer is formed on the outer surface of the bacteria, and the second coating layer is formed on the outer surface of said first coating layer, said first coating layer and said second coating layer comprising a same lipid of vegetable origin and selected from mono- and diglycerides of saturated fatty acids, polyglycerols esterified with saturated fatty acids and free saturated fatty acids.

2. The bacteria according to claim 1, wherein the lipids are saturated vegetable fats having a melting point from 35° C. to 85° C.

3. The bacteria according to claim 1, wherein the same lipid of vegetal origin is selected from a glycerides, C16-18 mono- and di- having CAS No. 85251-77-0, a polyglyceryl-6-distearate having a CAS No. 61725-93-7, a mixture of esters of glycerol and fatty acids C16-C18 and a hydrogenated vegetable fat of non-lauric origin.

4. The bacteria according claim 1, wherein the multilayer coating consists of the first coating layer and the second coating layer, and wherein the same lipid of vegetable origin comprises glycerides, C16-18 mono- and di- having CAS No. 85251-77-0.

5. The bacteria according to claim 1, wherein the multilayer coating consists of the first coating layer and the second coating layer, and wherein the same lipid of vegetal origin comprises polyglyceryl-6-distearate having a CAS No. 61725-93-7.

6. The bacteria according to claim 1, wherein the multilayer coating consists of the first coating layer, the second coating layer and a third coating layer, and wherein the first coating layer and the second coating layer comprise glycerides, C16-18 mono- and di- having CAS No. 85251-77-0 and the third coating layer comprises polyglyceryl-6-distearate having a CAS No. 61725-93-7, a mixture of esters of glycerol and fatty acids C16-C18 and a hydrogenated vegetable fat of non-lauric origin.

7. The bacteria according to claim 1, wherein said bacteria have a concentration from $1\times10^6$ to $1\times10^{11}$ CFU/g.

8. The bacteria according to claim 1, wherein the lipids are saturated vegetable fats having a melting point from 45 to 70° C.

9. The bacteria according to claim 1, wherein the multilayer coating consists of the first coating layer, the second coating layer and a third coating layer, and wherein, the first coating layer and the second coating layer comprise polyglyceryl-6-distearate having a CAS No. 61725-93-7 and the third coating layer comprises glycerides, C16-18 mono- and di- having CAS No. 85251-77-0, a mixture of esters of glycerol and fatty acids C16-C18 and a hydrogenated vegetable fat of non-lauric origin.

10. The bacteria according to claim 1, wherein said bacteria have a concentration from $1\times10^7$ to $1\times10^{10}$ CFU/g.

11. The bacteria according to claim 1, wherein said bacteria have a concentration from $1\times10^8$ to $1\times10^9$ CFU/g.

12. The bacteria according to claim 1, wherein said bacteria are within an aqueous solution or a product in a solid, powder or granular form.

13. The bacteria according to claim 1, wherein the hydrogenated vegetable fat of non-lauric origin has a maximal free fatty acids of 0.20% calculated as a percentage of oleic acid, a maximal peroxide value of 0.20 meqO$_2$/Kg of saturated fatty acids, a minimum solid fat percentage at 20° C. of 94% and a solid fat percentage at 40° C. ranging from a minimum of 94% to a maximum of 99%.

14. A food product or a medical device or a supplement product comprising the coated bacteria according claim 1.

15. The food product according to claim 14, wherein the bacteria are introduced into a food selected from:
powdered milk, in a quantity from 0.1 to 20% by weight relative to the weight of the food product;
fresh milk, in a quantity from 0.1 to 20% by weight relative to the weight of the food product;
butter or margarine, in a quantity from 0.1 to 20% by weight relative to the weight of the food product;
cream or yogurt, in a quantity from 0.1 to 20% by weight relative to the weight of the food product;
grated cheese, in a quantity from 0.1 to 20% by weight relative to the weight of the food product;
milk-flavoured custard for filling sweets, in a quantity from 0.1 to 20% by weight relative to the weight of the food product;
chocolate-flavoured custard for filling sweets, in a quantity from 0.1 to 20% by weight relative to the weight of the food product; and
apricot jam, in a quantity from 0.1 to 20% by weight relative to the weight of the food product.

16. The food product according to claim 15, wherein the bacteria are at a concentration from $1\times10^6$ to $1\times10^{11}$ CFU/g or $1\times10^7$ to $1\times10^{10}$ CFU/g or $1\times10^8$ to $1\times10^9$ CFU/g.

17. The food product according to claim 15, wherein the bacteria are introduced into the food in a quantity from 0.5 to 10% by weight, relative to the weight of the food.

18. The food product according to claim 15, wherein the bacteria are introduced into the food in a quantity from 1 to 5% by weight, relative to the weight of the food product.

19. A pharmaceutical composition comprising the bacteria according to claim 1 and at least one pharmaceutical active ingredient with antibiotic activity.

20. The pharmaceutical composition of claim 19, wherein the at least one pharmaceutical active ingredient is an antibiotic selected from the group comprising ciprofloxacin, erythromycin or ampicillin.

* * * * *